United States Patent
Chang et al.

(10) Patent No.: US 11,298,217 B2
(45) Date of Patent: Apr. 12, 2022

(54) POROUS DEVICES AND PROCESSES FOR PRODUCING SAME

(71) Applicant: Vertera Inc., Atlanta, GA (US)

(72) Inventors: Wei-Hsiang Chang, Duluth, GA (US); Stephen Lee Laffoon, Atlanta, GA (US); Christopher S. D. Lee, Atlanta, GA (US); David Lee Safranski, Atlanta, GA (US)

(73) Assignee: Vertera, Inc., Atlanta, GA (US)

( * ) Notice: Subject to any disclaimer, the term of this patent is extended or adjusted under 35 U.S.C. 154(b) by 261 days.

(21) Appl. No.: 16/524,541

(22) Filed: Jul. 29, 2019

(65) Prior Publication Data

US 2019/0343611 A1 Nov. 14, 2019

Related U.S. Application Data

(63) Continuation of application No. 15/854,746, filed on Dec. 26, 2017, now Pat. No. 10,405,962, which is a (Continued)

(51) Int. Cl.
 *A61F 2/07* (2013.01)
 *A61L 27/18* (2006.01)
 (Continued)

(52) U.S. Cl.
 CPC .............. *A61F 2/0077* (2013.01); *A61B 6/12* (2013.01); *A61B 6/50* (2013.01); *A61B 90/39* (2016.02);
 (Continued)

(58) Field of Classification Search
 CPC ........... A61F 2/0077; A61F 2210/0071; A61L 27/18; A61L 31/06
 See application file for complete search history.

(56) References Cited

U.S. PATENT DOCUMENTS

| 699,026 A | 12/1899 | Shaler |
|---|---|---|
| 3,059,275 A | 10/1962 | Vogt |

(Continued)

FOREIGN PATENT DOCUMENTS

| DE | 10054089 | 7/2002 |
|---|---|---|
| DE | 102006014174 | 9/2007 |

(Continued)

OTHER PUBLICATIONS

Dirienzo, Amy et al., Porous poly(para-phenylene) scaffolds for load-bearing orthopedic applications, Journal of the Mechanical Behavior of Biomedical Materials 30(2014)347-357.

(Continued)

*Primary Examiner* — Jason-Dennis N Stewart
(74) *Attorney, Agent, or Firm* — Hoffman Warnick LLC

(57) ABSTRACT

Devices and methods for making a polymer with a porous layer from a solid piece of polymer are disclosed. In various embodiments, the method includes heating a surface of a solid piece of polymer to a processing temperature and holding the processing temperature while displacing a porogen layer through the surface of the polymer to create a matrix layer of the solid polymer body comprising the polymer and the porogen layer. In at least one embodiment, the method also includes removing at least a portion of the layer of porogen from the matrix layer to create a porous layer of the solid piece of polymer.

20 Claims, 28 Drawing Sheets

Related U.S. Application Data continuation of application No. 15/362,223, filed on Nov. 28, 2016, now Pat. No. 9,848,973, which is a continuation of application No. 14/752,762, filed on Jun. 26, 2015, now Pat. No. 9,504,550, which is a continuation-in-part of application No. 14/587,856, filed on Dec. 31, 2014, now Pat. No. 9,085,665.

(60) Provisional application No. 62/017,834, filed on Jun. 26, 2014.

(51) Int. Cl.

| | | |
|---|---|---|
| *A61F 2/00* | (2006.01) | |
| *A61L 31/06* | (2006.01) | |
| *B29C 67/20* | (2006.01) | |
| *C08J 9/00* | (2006.01) | |
| *C08J 9/26* | (2006.01) | |
| *A61B 90/00* | (2016.01) | |
| *A61B 6/00* | (2006.01) | |
| *A61F 2/44* | (2006.01) | |
| *A61L 27/50* | (2006.01) | |
| *A61L 27/56* | (2006.01) | |
| *B29C 44/04* | (2006.01) | |
| *B29C 44/34* | (2006.01) | |
| *A61B 6/12* | (2006.01) | |
| *B29K 71/00* | (2006.01) | |
| *B29L 31/00* | (2006.01) | |

(52) U.S. Cl.
CPC .............. *A61F 2/44* (2013.01); *A61L 27/18* (2013.01); *A61L 27/50* (2013.01); *A61L 27/56* (2013.01); *A61L 31/06* (2013.01); *B29C 44/0461* (2013.01); *B29C 44/3415* (2013.01); *B29C 67/202* (2013.01); *C08J 9/0085* (2013.01); *C08J 9/26* (2013.01); *A61B 2090/3966* (2016.02); *A61F 2002/0081* (2013.01); *A61F 2002/0086* (2013.01); *A61F 2210/0071* (2013.01); *A61F 2250/0098* (2013.01); *A61L 2430/38* (2013.01); *B29K 2071/00* (2013.01); *B29L 2031/753* (2013.01); *B29L 2031/7546* (2013.01); *C08J 2201/0446* (2013.01); *C08J 2371/00* (2013.01)

(56) References Cited

U.S. PATENT DOCUMENTS

| | | |
|---|---|---|
| 3,445,553 A | 5/1969 | Hardigg |
| 3,679,538 A | 7/1972 | Druin |
| 3,924,995 A | 12/1975 | Crooks et al. |
| 3,947,212 A | 3/1976 | Griner et al. |
| 4,043,733 A | 8/1977 | De Mets |
| 4,164,794 A | 8/1979 | Spector et al. |
| 4,351,069 A | 9/1982 | Ballintyn et al. |
| 4,487,731 A | 12/1984 | Kobayashi |
| 4,549,920 A | 10/1985 | Cogswell et al. |
| 4,764,427 A | 8/1988 | Hara et al. |
| 4,778,469 A | 10/1988 | Lin et al. |
| 4,828,479 A | 5/1989 | Pleasant |
| 4,863,604 A | 9/1989 | Lo et al. |
| 4,969,906 A | 11/1990 | Kronman |
| 5,100,590 A | 3/1992 | Ruhlin |
| 5,171,281 A | 12/1992 | Parsons et al. |
| 5,326,354 A | 7/1994 | Kwarteng |
| 5,453,237 A | 9/1995 | Padovani |
| 5,458,820 A | 10/1995 | Lefebvre |
| 5,503,278 A | 4/1996 | Ishmael |
| 5,707,578 A | 1/1998 | Johnson et al. |
| 5,865,845 A | 2/1999 | Thalgott |
| 5,885,691 A | 3/1999 | Breezer et al. |
| 5,981,619 A | 11/1999 | Shikinami et al. |
| 6,149,688 A | 11/2000 | Brosnahan et al. |
| 6,183,873 B1 | 2/2001 | Clarke |
| 6,187,329 B1 | 2/2001 | Agrawal et al. |
| 6,241,771 B1 | 6/2001 | Gresser et al. |
| 6,277,149 B1 | 8/2001 | Boyle et al. |
| 6,306,424 B1 | 10/2001 | Vyakarnam et al. |
| 6,333,029 B1 | 12/2001 | Vyakarnam et al. |
| 6,371,904 B1 | 4/2002 | Sirimanne et al. |
| 6,387,311 B1 | 5/2002 | Lacour et al. |
| 6,458,308 B1 | 10/2002 | Kato |
| 6,503,278 B1 | 1/2003 | Pohjonen et al. |
| 6,673,075 B2 | 1/2004 | Santilli |
| 6,689,608 B1 | 2/2004 | Mikos et al. |
| 6,719,942 B1 | 4/2004 | Triplett et al. |
| D530,423 S | 10/2006 | Miles et al. |
| 7,425,288 B2 | 9/2008 | Flodin et al. |
| 7,575,759 B2 | 8/2009 | Murphy et al. |
| 7,723,395 B2 | 5/2010 | Ringeisen et al. |
| D623,747 S | 9/2010 | Horton |
| 7,807,260 B2 | 10/2010 | Nadella et al. |
| 7,819,650 B2 | 10/2010 | Meskendahl et al. |
| D631,967 S | 2/2011 | Horton |
| 7,879,109 B2 | 2/2011 | Borden et al. |
| 7,964,206 B2 | 6/2011 | Suokas et al. |
| 8,029,575 B2 | 10/2011 | Borden |
| 8,110,007 B2 | 2/2012 | Borden |
| 8,177,854 B2 | 5/2012 | Borden |
| 8,206,450 B2 | 6/2012 | Henry et al. |
| 8,377,548 B2 | 2/2013 | Nadella et al. |
| 8,383,024 B2 | 2/2013 | Morrissette et al. |
| 8,389,588 B2 | 3/2013 | Ringeisen et al. |
| 8,414,654 B1 | 4/2013 | Ganey |
| 8,445,554 B2 | 5/2013 | Ringeisen et al. |
| 8,454,696 B2 | 6/2013 | Borden |
| 8,530,560 B2 | 9/2013 | Kerr et al. |
| D692,136 S | 10/2013 | Tyber |
| 8,609,127 B2 | 12/2013 | Avage-Erickson |
| 8,647,393 B2 | 2/2014 | Marshall et al. |
| 8,673,018 B2 | 3/2014 | Walls |
| 8,679,191 B2 | 3/2014 | Borden et al. |
| 8,715,286 B2 | 5/2014 | Borden |
| 8,715,366 B2 | 5/2014 | Borden |
| 8,821,912 B2 | 9/2014 | Crudden et al. |
| 8,864,831 B2 | 10/2014 | Lee et al. |
| 8,864,839 B2 | 10/2014 | Ganey |
| 8,877,331 B2 | 11/2014 | Nadella et al. |
| 8,888,860 B2 | 11/2014 | Taylor |
| 8,998,987 B2 | 4/2015 | Wallick |
| 9,015,922 B2 | 4/2015 | Ganey |
| D735,859 S | 8/2015 | Palinchik et al. |
| D735,860 S | 8/2015 | Palinchik et al. |
| D735,861 S | 8/2015 | Embleton et al. |
| D736,384 S | 8/2015 | Palinchik et al. |
| 9,132,576 B2 | 9/2015 | Crudden et al. |
| 9,254,193 B2 | 2/2016 | Kerr et al. |
| 9,308,076 B2 | 4/2016 | Ringeisen et al. |
| 9,308,297 B2 | 4/2016 | Kerr et al. |
| 9,345,817 B2 | 5/2016 | Papangelou et al. |
| 9,353,235 B1 | 5/2016 | Chang et al. |
| 9,393,121 B2 | 7/2016 | Taylor |
| 9,439,779 B2 | 9/2016 | Zhang et al. |
| 9,456,905 B2 | 10/2016 | Borden et al. |
| 9,498,922 B2 | 11/2016 | Chang et al. |
| 9,504,550 B2 | 11/2016 | Chang et al. |
| 9,545,315 B2 | 1/2017 | Borden |
| 9,592,206 B2 | 3/2017 | Walls |
| 9,700,431 B2 | 7/2017 | Nebosky et al. |
| D794,796 S | 8/2017 | Lin |
| 2001/0015152 A1 | 8/2001 | Dohr et al. |
| 2001/0020757 A1 | 9/2001 | Fried et al. |
| 2003/0086973 A1 | 5/2003 | Sowden et al. |
| 2003/0134067 A1 | 7/2003 | Garelli |
| 2003/0138516 A1 | 7/2003 | Hess et al. |
| 2004/0026811 A1 | 2/2004 | Murphy et al. |
| 2004/0138058 A1 | 7/2004 | Sambasivan et al. |
| 2004/0152974 A1 | 8/2004 | Solomon |
| 2004/0164442 A1 | 8/2004 | Olsson et al. |
| 2004/0171924 A1 | 9/2004 | Mire et al. |
| 2004/0234636 A1 | 11/2004 | Murata et al. |

(56) References Cited

U.S. PATENT DOCUMENTS

| | | |
|---|---|---|
| 2005/0012298 A1 | 1/2005 | Dal Pra et al. |
| 2005/0220932 A1 | 10/2005 | van der Eerden et al. |
| 2005/0225008 A1 | 10/2005 | Deardurff et al. |
| 2005/0246021 A1 | 11/2005 | Ringeisen et al. |
| 2006/0094852 A1 | 5/2006 | Yuan et al. |
| 2007/0191962 A1 | 8/2007 | Jones et al. |
| 2007/0266542 A1 | 11/2007 | Melsheimer |
| 2007/0275863 A1 | 11/2007 | Whitmarsh |
| 2008/0032112 A1 | 2/2008 | Hirata et al. |
| 2008/0071382 A1 | 3/2008 | Kumar et al. |
| 2008/0161927 A1 | 7/2008 | Savage et al. |
| 2008/0185748 A1 | 8/2008 | Kalkanoglu |
| 2008/0185752 A1 | 8/2008 | Cerwin et al. |
| 2008/0206297 A1 | 8/2008 | Roeder et al. |
| 2008/0208325 A1 | 8/2008 | Helmus et al. |
| 2008/0211128 A1 | 9/2008 | Lucier et al. |
| 2009/0045119 A1 | 2/2009 | Hosoya et al. |
| 2009/0104420 A1 | 4/2009 | Nadella et al. |
| 2009/0222091 A1 | 9/2009 | Morrissette et al. |
| 2010/0040902 A1 | 2/2010 | Mizrahi |
| 2010/0042218 A1 | 2/2010 | Nebosky et al. |
| 2010/0042226 A1 | 2/2010 | Nebosky et al. |
| 2010/0087925 A1 | 4/2010 | Kostuik et al. |
| 2010/0151114 A1 | 6/2010 | Parrott |
| 2010/0173036 A1 | 7/2010 | Haynes et al. |
| 2010/0225033 A1 | 9/2010 | Kwasniewski et al. |
| 2010/0234966 A1 | 9/2010 | Lo |
| 2010/0256804 A1 | 10/2010 | Freeman |
| 2010/0268337 A1 | 10/2010 | Gordon et al. |
| 2011/0012280 A1 | 1/2011 | Deslauriers et al. |
| 2011/0015743 A1 | 1/2011 | Deslauriers et al. |
| 2011/0022181 A1 | 1/2011 | Kasahara et al. |
| 2011/0144480 A1 | 6/2011 | Lu et al. |
| 2011/0177320 A1 | 7/2011 | Mehrabi et al. |
| 2011/0230970 A1 | 9/2011 | Lynn et al. |
| 2011/0290674 A1 | 12/2011 | Shanley |
| 2012/0004673 A1 | 1/2012 | Noishiki |
| 2012/0040037 A1 | 2/2012 | Kwasniewski et al. |
| 2012/0077010 A1 | 3/2012 | Manesis et al. |
| 2012/0150299 A1 | 6/2012 | Ergun et al. |
| 2012/0215310 A1 | 8/2012 | Sharp et al. |
| 2012/0310137 A1 | 12/2012 | Silvestrini |
| 2012/0323339 A1 | 12/2012 | Olalde Graells et al. |
| 2013/0053688 A1 | 2/2013 | Watschke et al. |
| 2013/0065981 A1 | 3/2013 | Nadella et al. |
| 2013/0119584 A1 | 5/2013 | Vantrease |
| 2013/0164403 A1 | 6/2013 | Boogers et al. |
| 2013/0171443 A1 | 7/2013 | Morrissette et al. |
| 2013/0178900 A1 | 7/2013 | Fallin et al. |
| 2013/0211541 A1 | 8/2013 | Kerr et al. |
| 2013/0282135 A1 | 10/2013 | Sun et al. |
| 2013/0330394 A1 | 12/2013 | Ponticiello et al. |
| 2013/0345827 A1 | 12/2013 | Wallick |
| 2014/0010911 A1 | 1/2014 | Rushing, Sr. |
| 2014/0102161 A1 | 4/2014 | Stewart |
| 2014/0236299 A1 | 8/2014 | Roeder et al. |
| 2014/0277461 A1 | 9/2014 | Nebosky et al. |
| 2014/0324213 A1 | 10/2014 | Stewart |
| 2014/0346716 A1 | 11/2014 | Zhang |
| 2015/0066152 A1 | 3/2015 | Slocum, Jr. et al. |
| 2015/0164619 A1 | 6/2015 | Patel et al. |
| 2015/0240042 A1 | 8/2015 | Nguyen et al. |
| 2015/0257869 A1 | 9/2015 | Borden |
| 2015/0265745 A1 | 9/2015 | Borden |
| 2015/0373381 A1 | 12/2015 | Rouhana, Jr. |
| 2016/0038289 A1 | 2/2016 | Noble |
| 2016/0128823 A1 | 5/2016 | Kerr et al. |
| 2016/0166301 A1 | 6/2016 | Papangelou et al. |
| 2016/0166373 A9 | 6/2016 | Borden |
| 2016/0166386 A1 | 6/2016 | Gerber et al. |
| 2016/0184483 A1 | 6/2016 | Kerr et al. |
| 2016/0199193 A1 | 7/2016 | Willis et al. |
| 2016/0228615 A1 | 8/2016 | Kasahara et al. |
| 2016/0237236 A1 | 8/2016 | Chang et al. |
| 2016/0361837 A1 | 12/2016 | Hayes et al. |
| 2017/0136156 A1 | 5/2017 | Walls |
| 2019/0270225 A1 | 9/2019 | Takano et al. |

FOREIGN PATENT DOCUMENTS

| | | |
|---|---|---|
| EP | 0512401 | 11/1992 |
| EP | 0714869 | 6/1996 |
| EP | 1162047 | 12/2001 |
| FR | 1171658 | 1/1959 |
| GB | 829811 | 3/1960 |
| WO | WO1997014377 | 4/1997 |
| WO | WO1999064361 | 12/1999 |
| WO | WO2002068373 | 9/2002 |
| WO | WO2003024626 | 3/2003 |
| WO | WO2003074227 | 9/2003 |
| WO | WO2003080119 | 10/2003 |
| WO | WO2004020362 | 3/2004 |
| WO | WO2004082333 | 9/2004 |
| WO | WO2007090131 | 8/2007 |
| WO | WO2016051326 | 4/2016 |

OTHER PUBLICATIONS

Evans, Nathan et al. High-strength, surface-porous polyether-ether-ketone for load-bearing orthopedic implants, Acta Biomaterialia 13 (2015) 159-167.

FortiCore® Cervical—Nanovis Inc. Retrieved Mar. 10, 2016, from http://www.nanovisinc.com/forticore-cervical/.

Hitachi, "DSC Measurement of Polypropolene", Aug. 2008, Hitachi High-Tech Science Corporation, TA No. 86, pp. 1-2.

International Preliminary Search Report on Patentability for International Application No. PCT/US2009/047286 filed Jun. 12, 2009.

International Search Report and Written Opinion for International Application No. PCT/US2009/047286 filed Jun. 12, 2009.

International Search Report and Written Opinion for International Application No. PCT/US2013/055655 filed Aug. 20, 2013.

International Search Report and Written Opinion for International Application No. PCT/US2013/055656 filed Aug. 20, 2013.

International Search Report and Written Opinion dated Sep. 23, 2015 in related PCT application No. PCT/US2015/038181.

Landy, Bonnie et al., Mechanical and in vitro investigation of a porous PEEK foam for medical device implants, J Appl Biomater Funct Mater 2013; 11 (1): 35-44.

Non-Final Office Action dated Mar. 3, 2016 in related U.S. Appl. No. 14/985,206.

Non-Final Office Action dated Mar. 4, 2016 in related U.S. Appl. No. 14/985,226.

Notice of Allowance in related U.S. Appl. No. 14/985,226 dated Jul. 15, 2016.

Siddiq, Abdur et al., Porous poly-ether ether ketone (PEEK) manufactured by a novel powder route using near-spherical salt bead porogens: Characterisation and mechanical properties, Materials Science and Engineering C 47 (2015) 180-188.

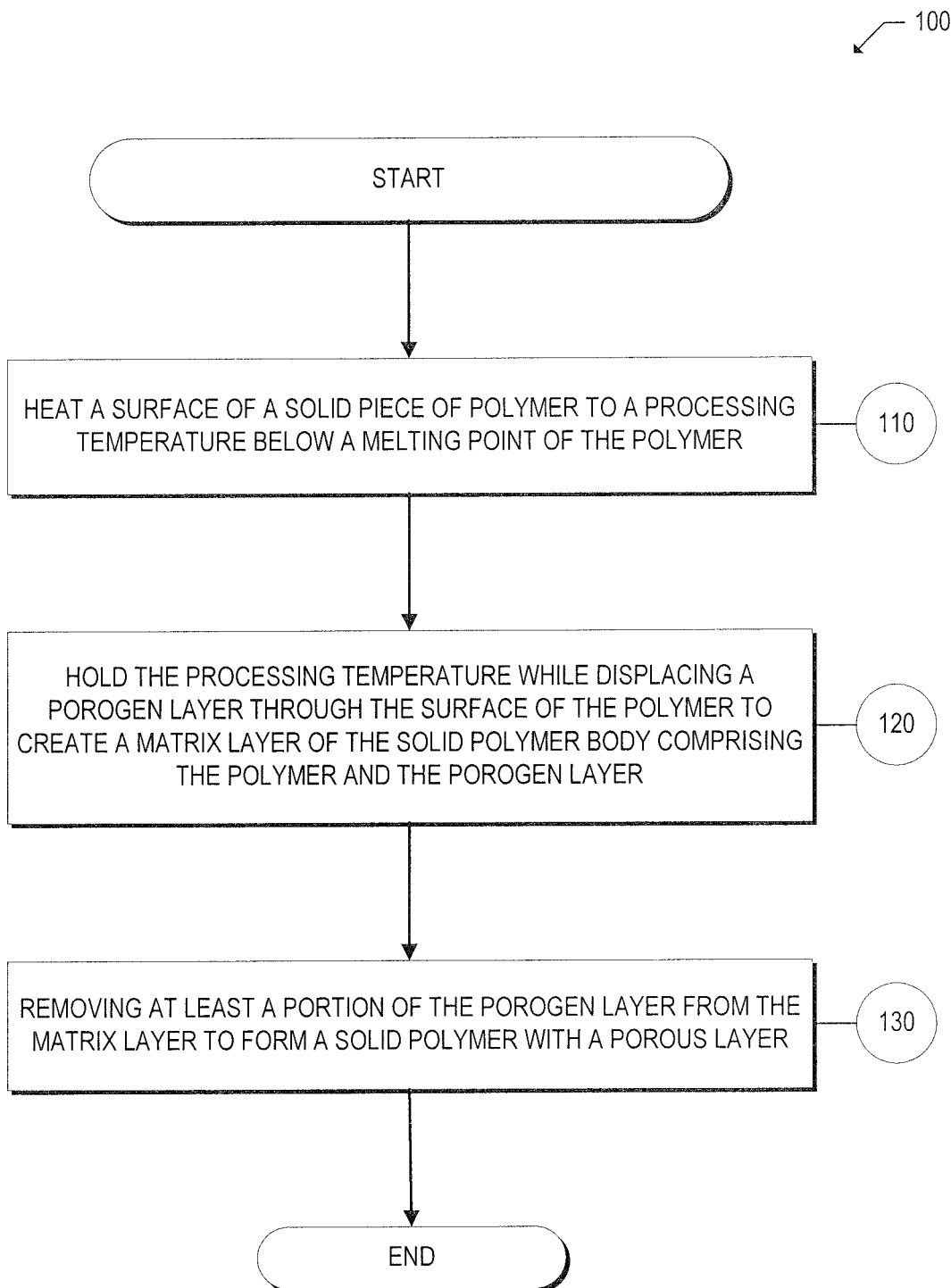
FIG. 1: *EXEMPLARY PROCESS*

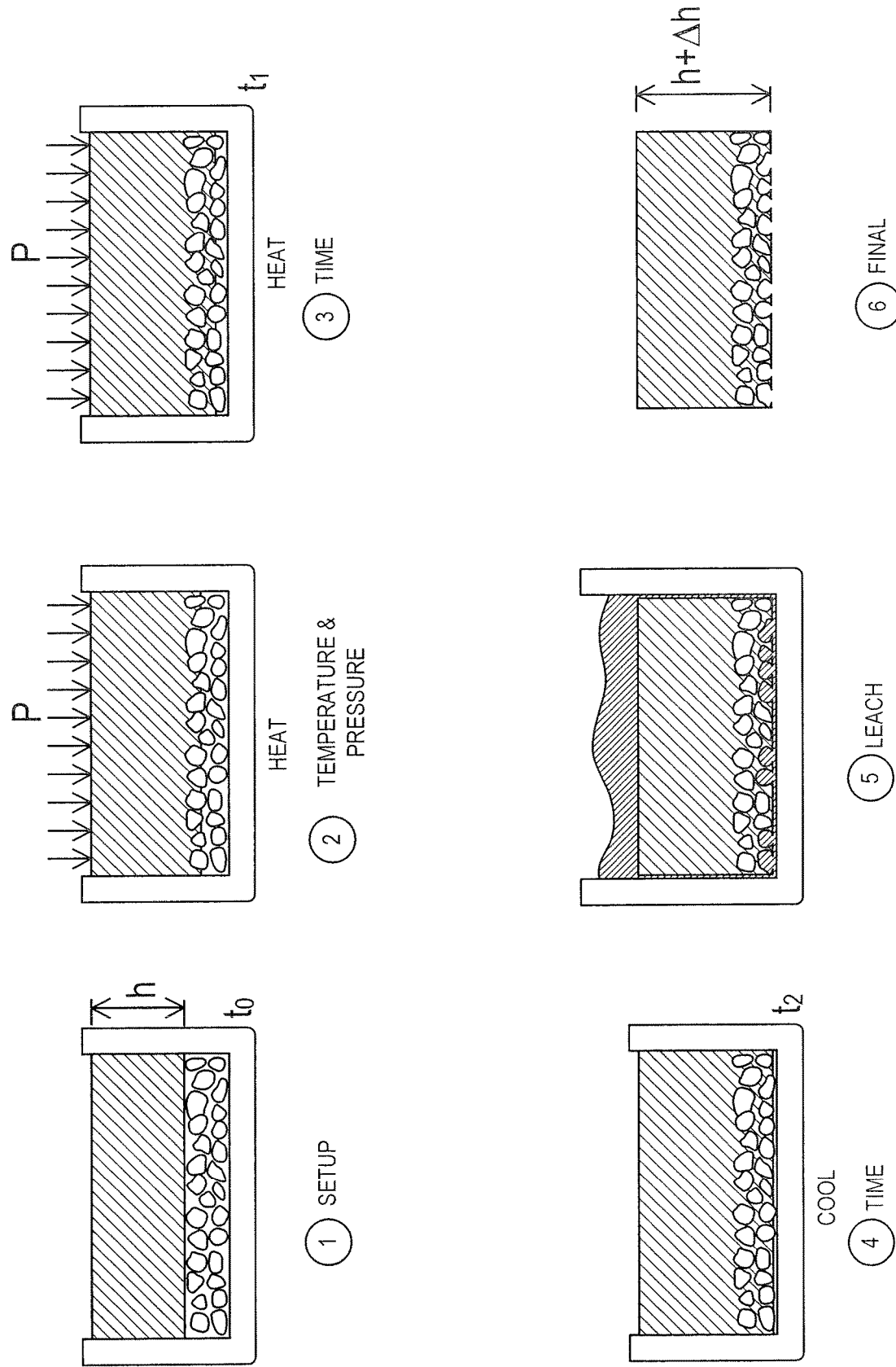

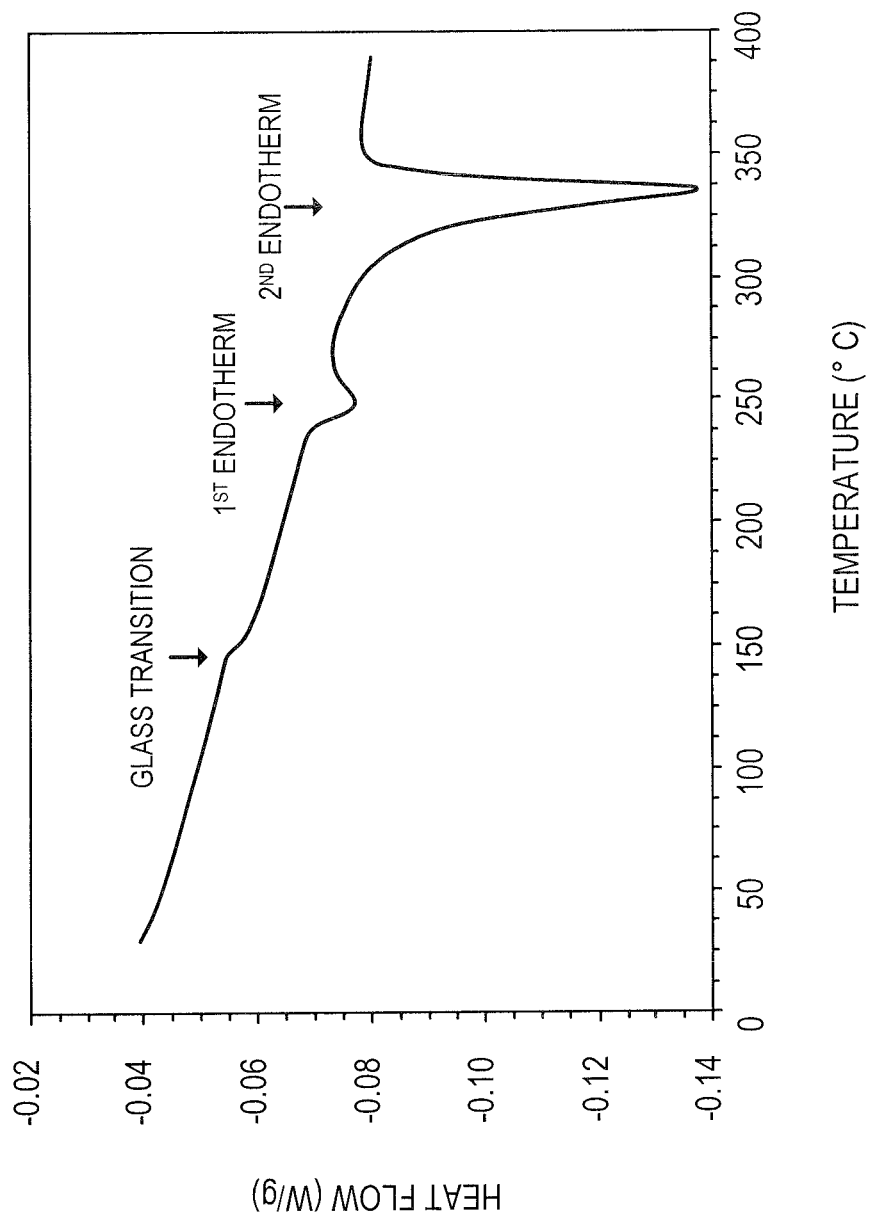
FIG. 3: DIFFERENTIAL SCANNING CALORIMETRY SCAN OF PEEK

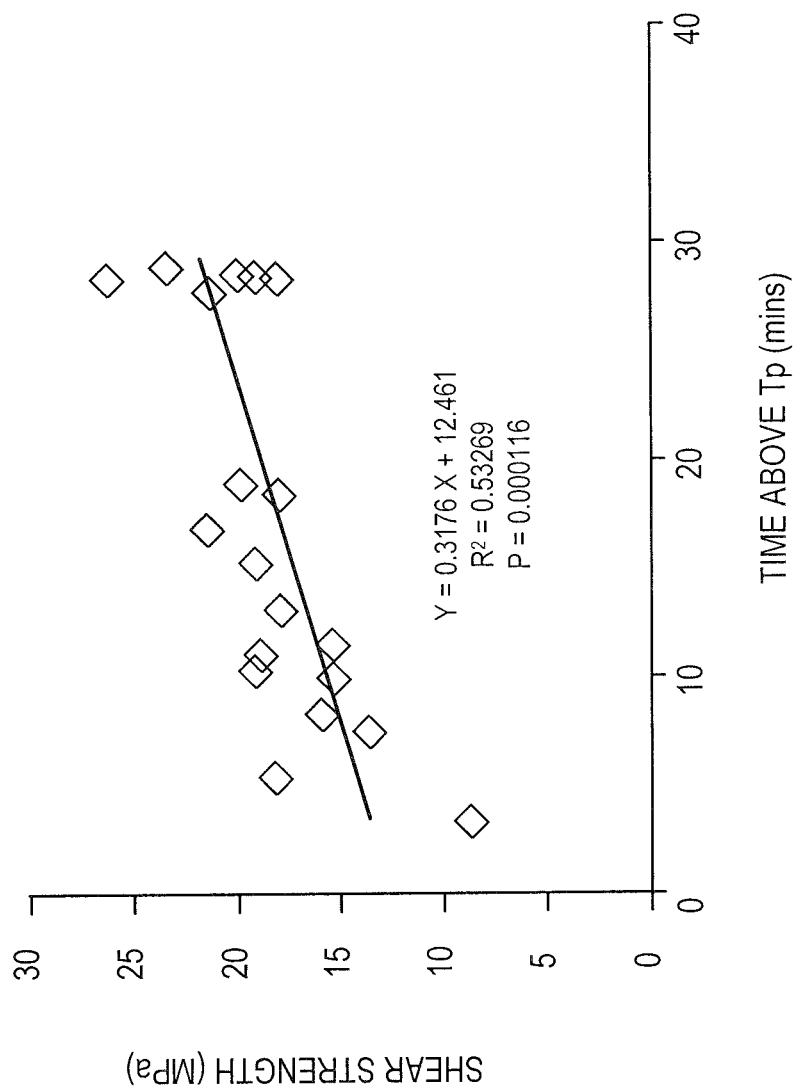
FIG. 4A: EXEMPLARY SHEAR STRENGTH V. TIME PLOT 1

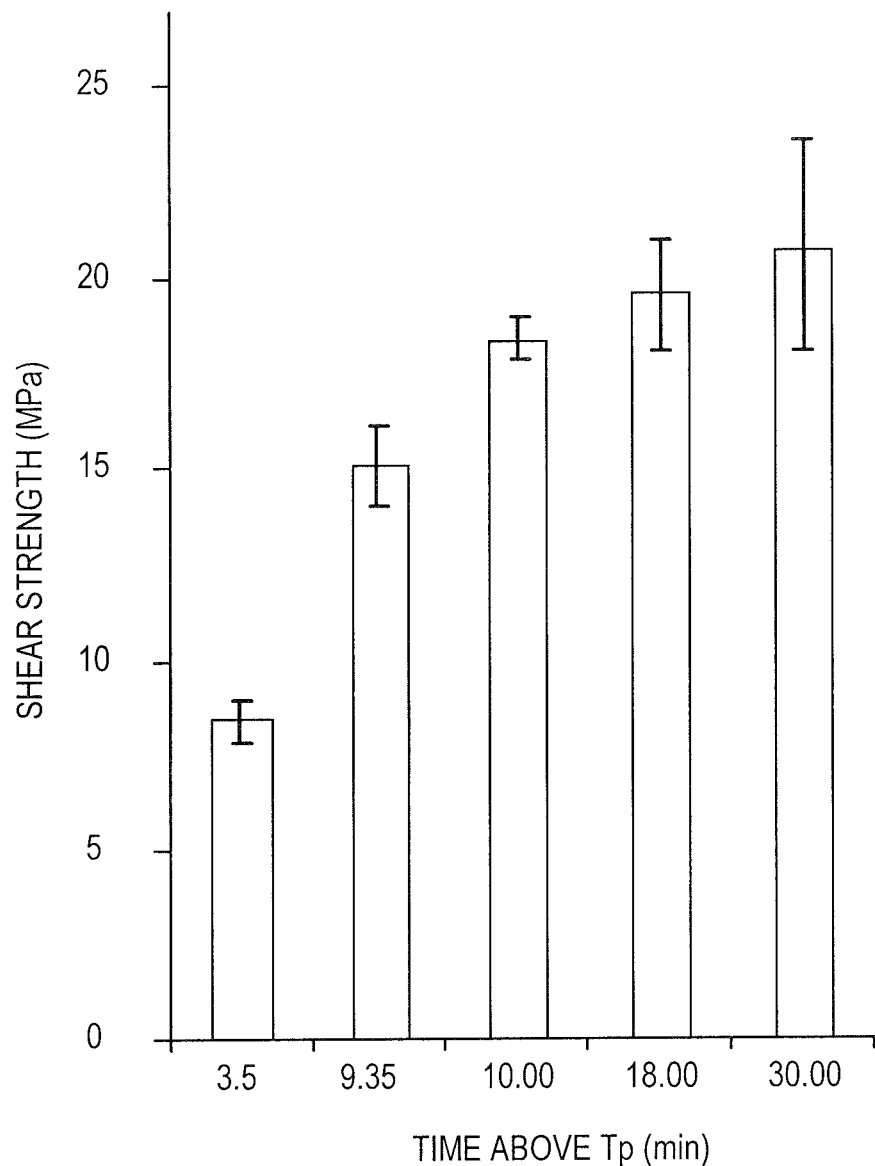
FIG. 4B: *EXEMPLARY SHEAR STRENGTH V. TIME BAR GRAPH 1*

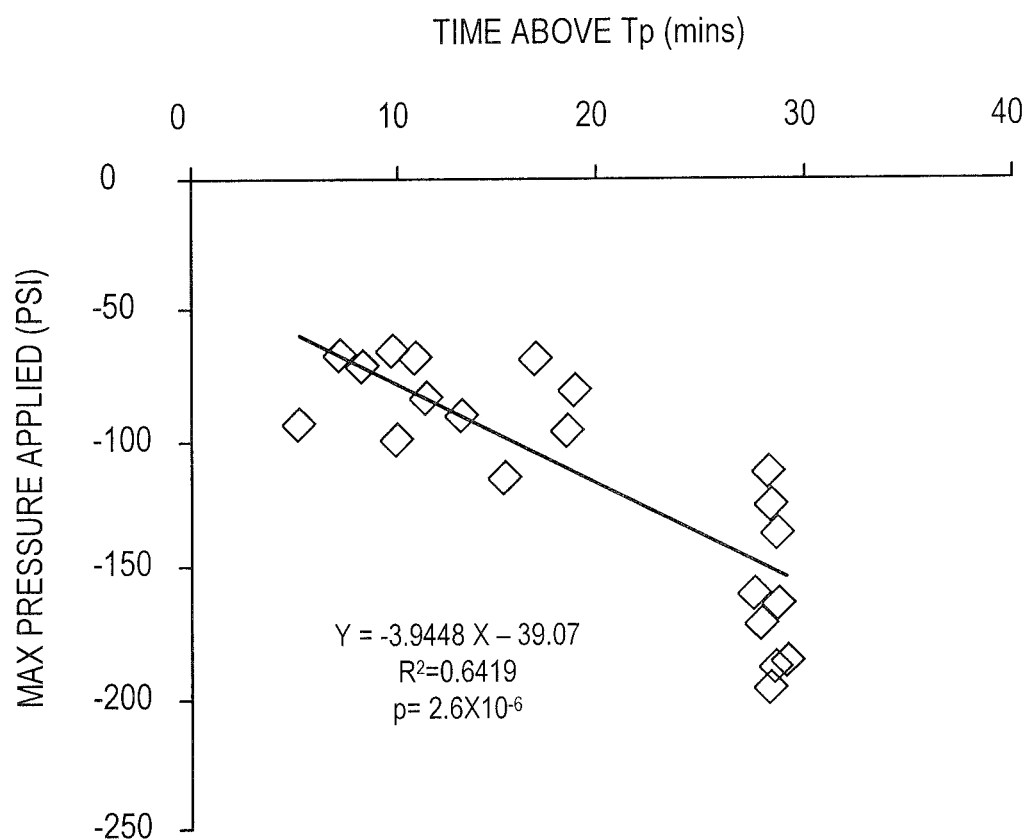
FIG. 4C: *EXEMPLARY MAX FLOW PRESSURE V. TIME PLOT 1*

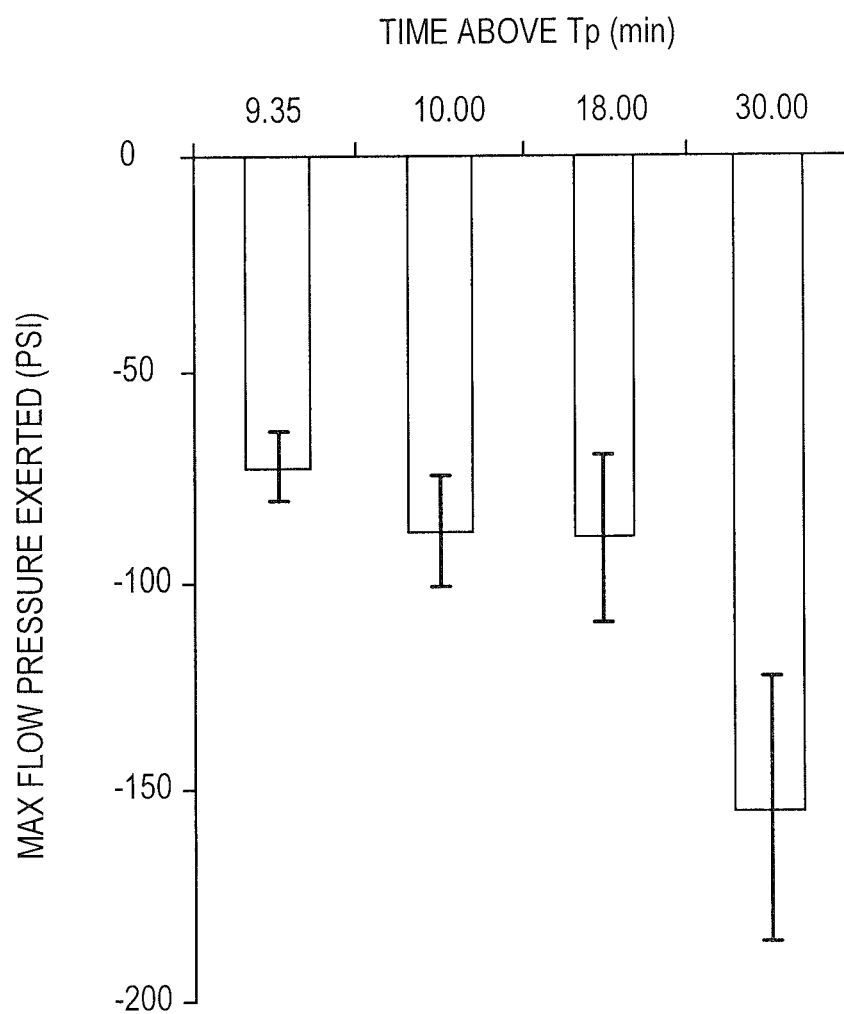
FIG. 4D: *EXEMPLARY MAX FLOW PRESSURE V. TIME BAR GRAPH 1*

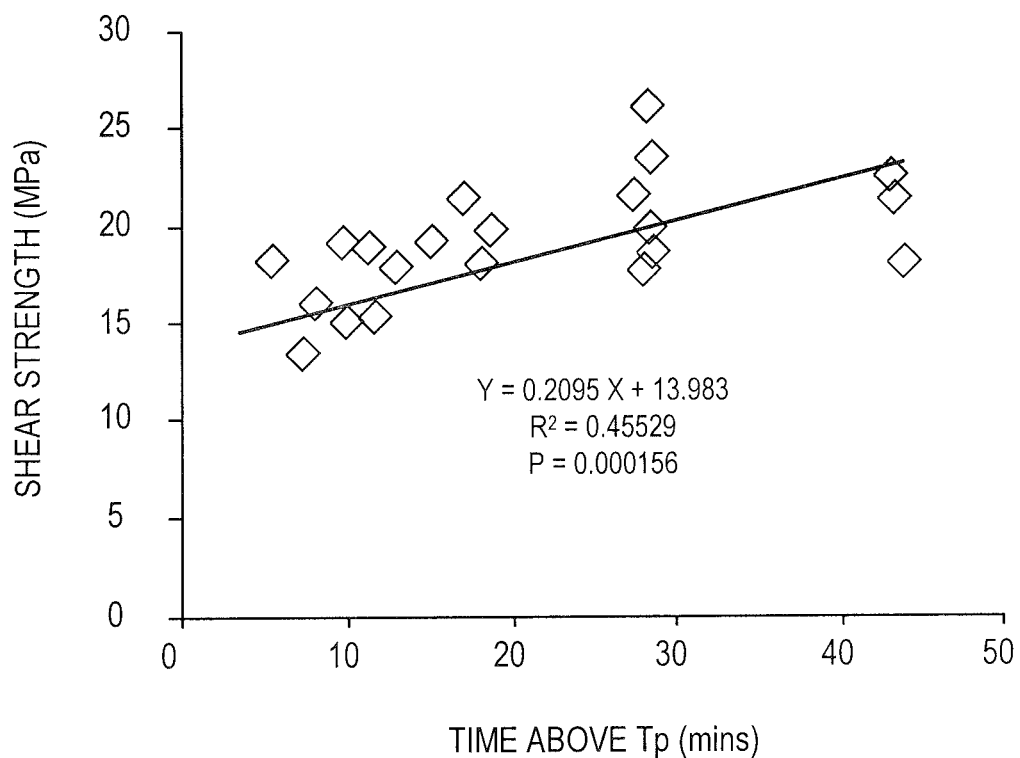
FIG. 5A: *EXEMPLARY SHEAR STRENGTH V. TIME PLOT 2*

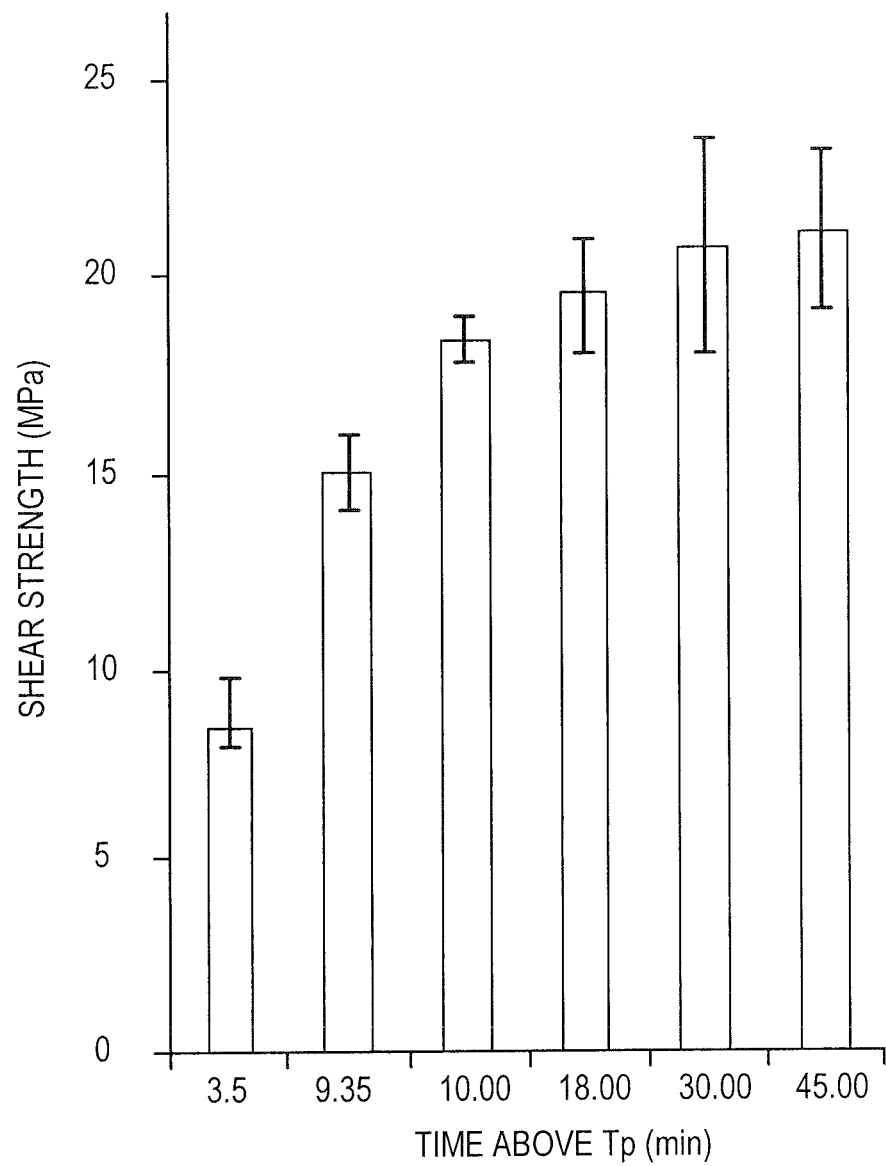
FIG. 5B: *EXEMPLARY SHEAR STRENGTH V. TIME BAR GRAPH 2*

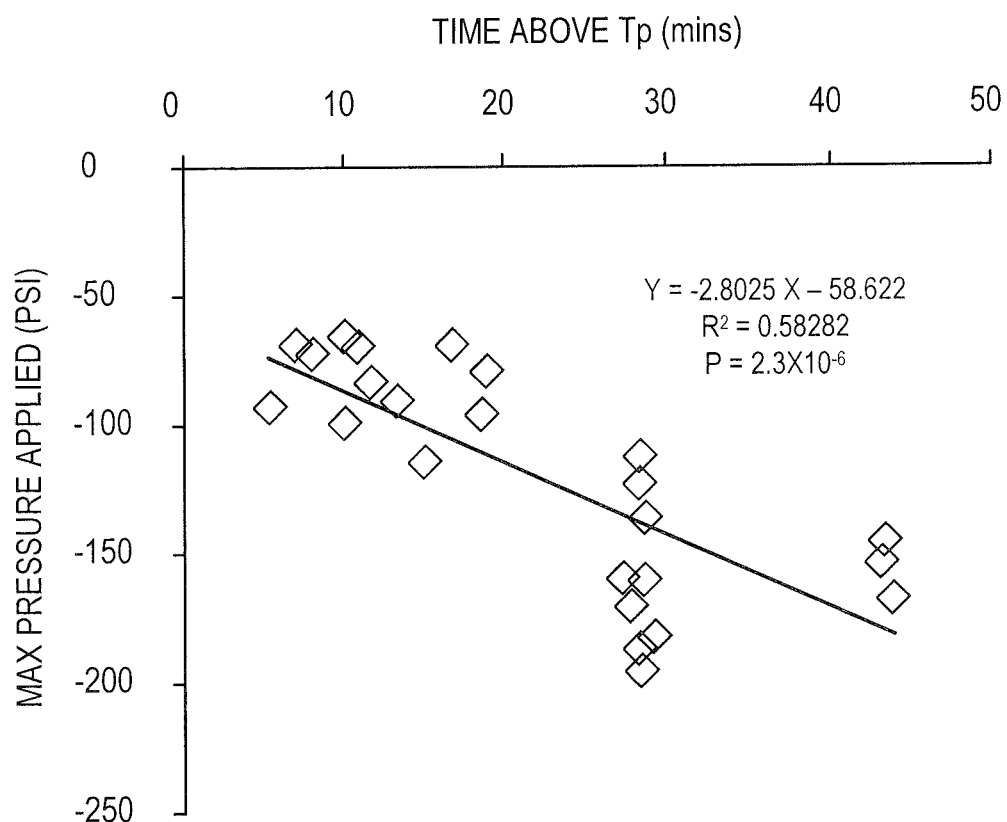
FIG. 5C: *EXEMPLARY MAX FLOW PRESSURE V. TIME PLOT 2*

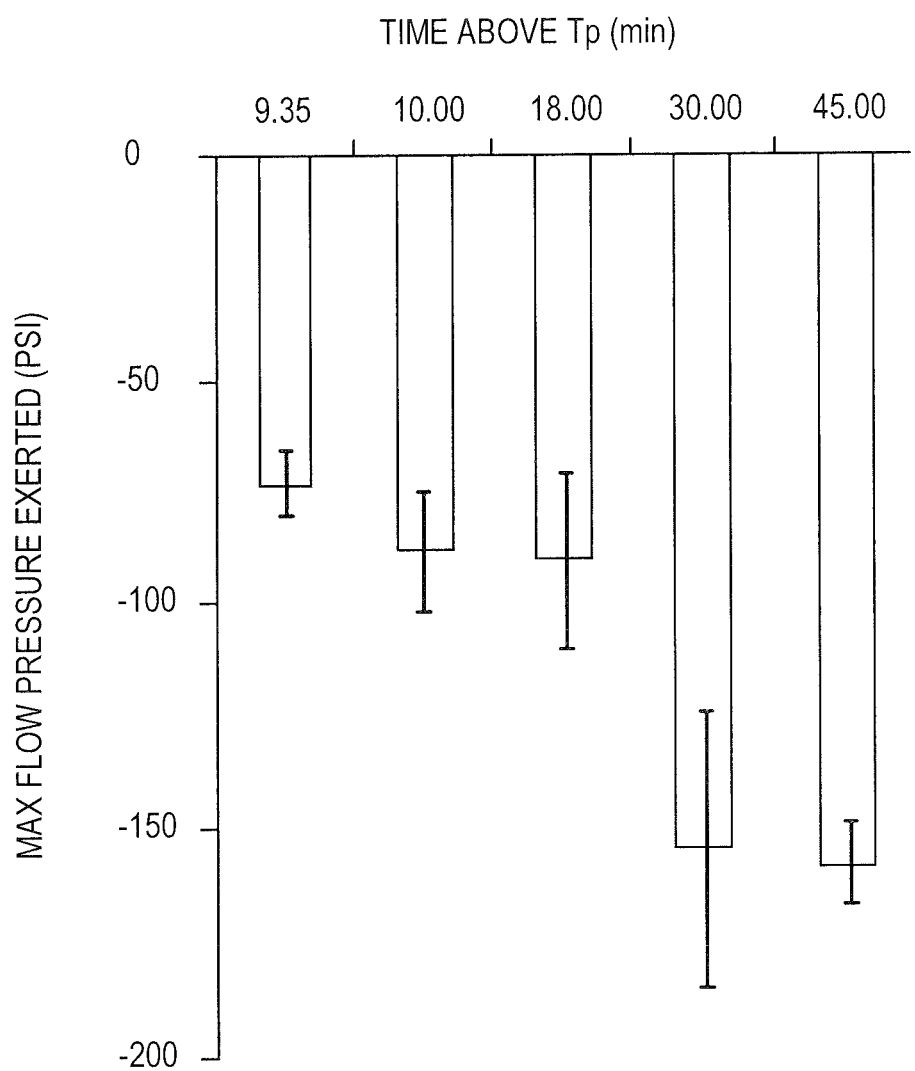
FIG. 5D: *EXEMPLARY MAX FLOW PRESSURE V. TIME BAR GRAPH 2*

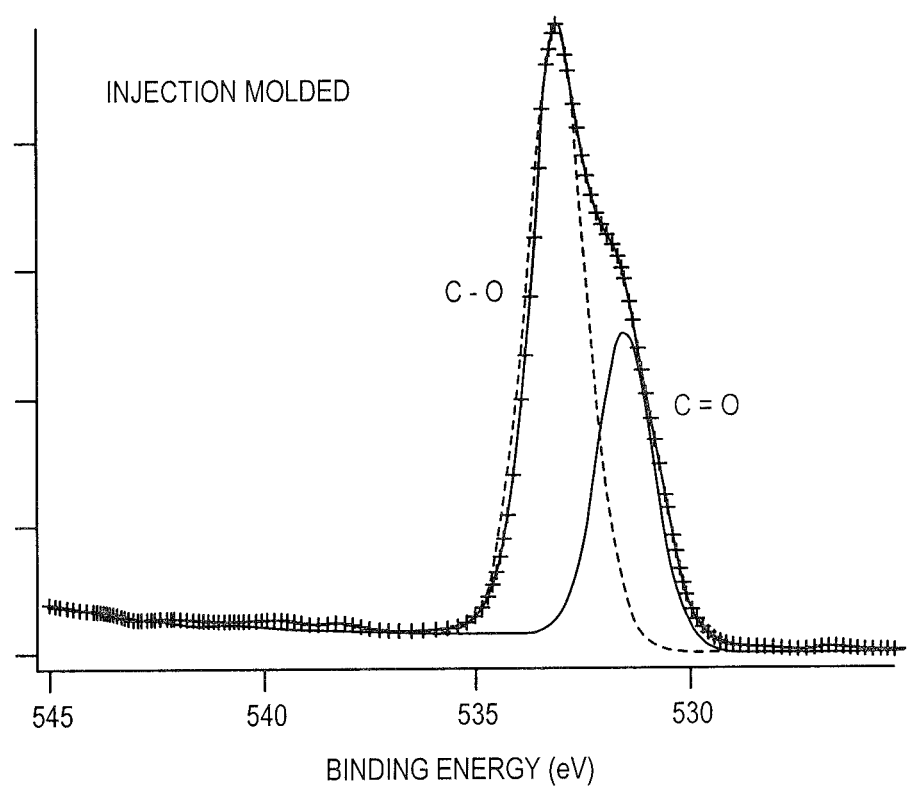
FIG. 6A: *EXEMPLARY XPS O1s Spectra of Injection Molded PEEK*

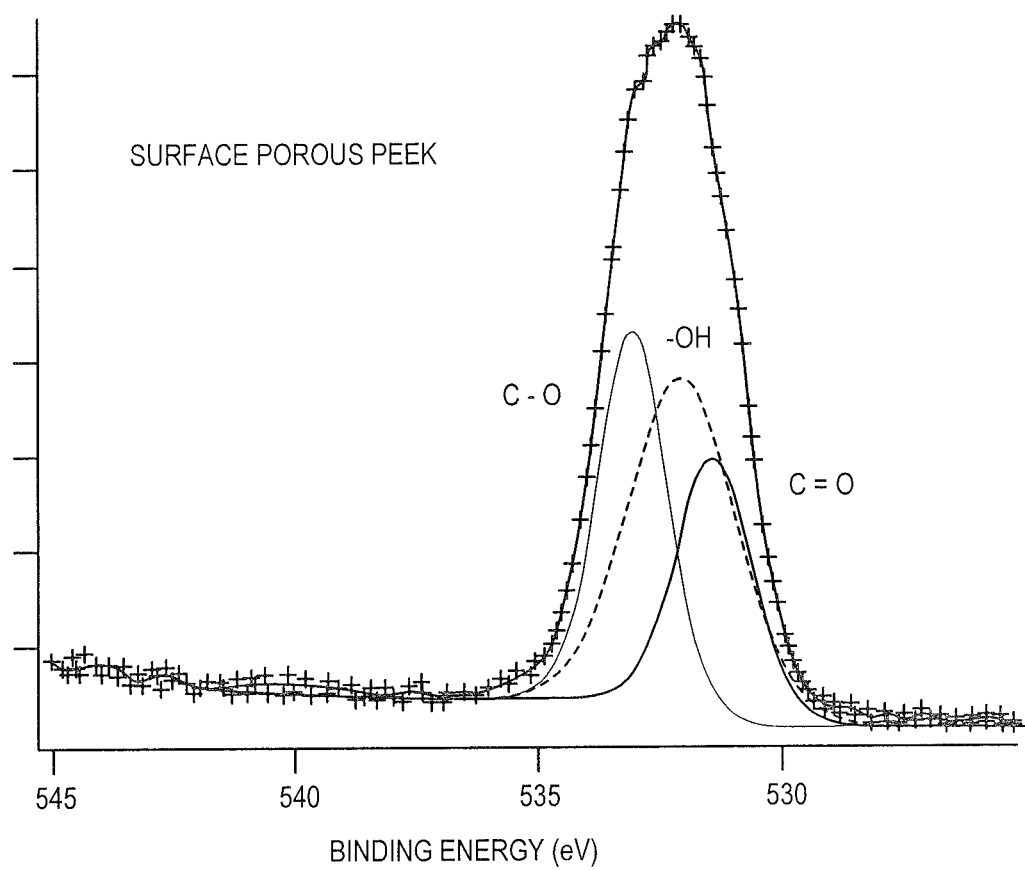
FIG. 6B: *EXEMPLARY XPS O1s Spectra of Surface Porous PEEK*

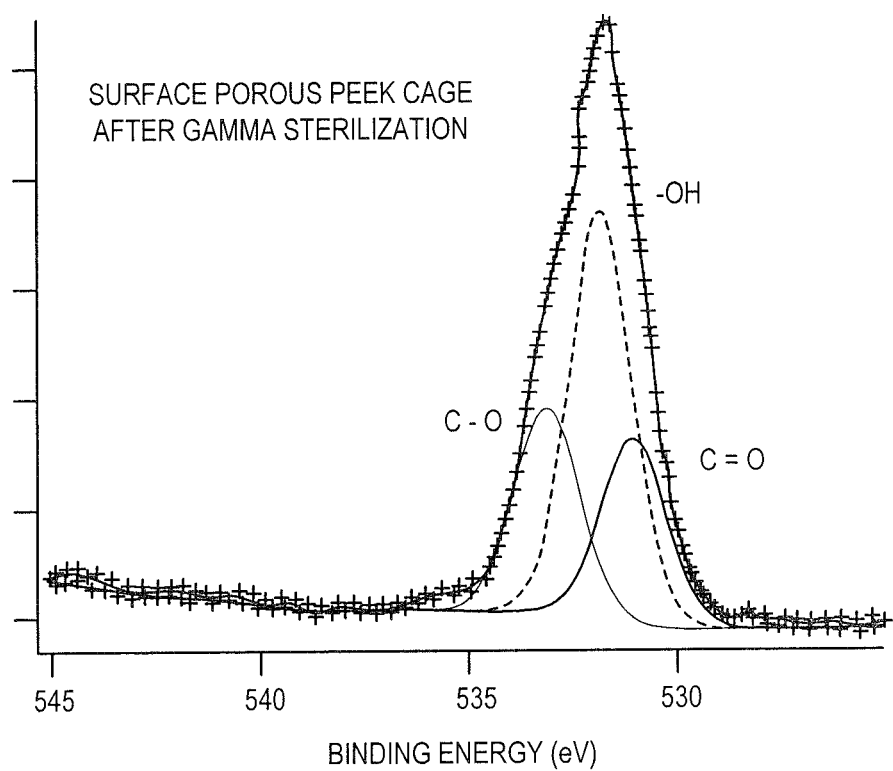
FIG. 6C: *EXEMPLARY XPS O1s Spectra of Surface Porous PEEK After Gamma Sterilization*

| SAMPLE | ETHER (AT%) | HYDROXYL (AT%) | KETONE (AT%) |
|---|---|---|---|
| INJECTION MOLDED PEEK | 65.65 ± 4.68 | 0 | 34.34 ± 4.68 |
| SURFACE POROUS PEEK | 31.48 ± 10.83 | 48.42 ± 14.9 | 20.09 ± 6.98 |
| GAMMA SURFACE POROUS PEEK CAGE | 28.95 ± 3.28 | 50.50 ± 2.98 | 20.53 ± 2.97 |
| EXTRUDED PEEK | 70.06 ± 3.5 | 0 | 29.93 ± 3.5 |

FIG. 6D: *EXEMPLARY XPS O1s Spectra Ratios*

| SAMPLE | CARBON AT% | OXYGEN AT% |
|---|---|---|
| INJECTION MOLDED PEEK | 79.97 ± 1.47 | 20.02 ± 1.47 |
| SURFACE POROUS PEEK | 79.82 ± 2.28 | 20.18 ±2.28 |
| GAMMA SURFACE POROUS PEEK CAGE | 84.17 ±0.94 | 15.83 ±0.94 |
| EXTRUDED PEEK | 84.39 ± 1.25 | 15.6 ± 1.25 |

FIG. 6E: *EXEMPLARY XPS O1s Elemental Ratios*

| SAMPLE | CONTACT ANGLE (°) |
|---|---|
| SURFACE POROUS PEEK CAGE | 0 |
| INJECTION MOLDED PEEK | 74.33 ± 2.2 |
| EXTRUDED PEEK | 80.87 ± 6.28 |
| PEEK AGAINST PACKED SALT WITHOUT PRESSURE | 49.49 ± 6.78 |
| PEEK AGAINST PACKED SALT WITH PRESSURE | 26.5 ± 2.06 |
| PEEK AGAINST SINGLE CRYSTAL SALT | 51.9 ± 17.13 |
| PEEK THERMALLY TREATED WITHOUT SALT | 78.41 ±3.41 |

FIG. 7A: *EXEMPLARY Wettability Data*

| SAMPLE | Ra(μm) |
|---|---|
| SALT CRYSTALS | 0.104 ± 0.076 |
| SURFACE POROUS PEEK CAGE | 1.67 ± 0.415 |
| EXTRUDED PEEK | 0.045 ± 0.029 |
| PEEK THERMALLY TREATED 340C AGAINST SINGLE CRYSTAL SALT | 0.085 ±0.055 |
| PEEK THERMALLY TREATED 340C AIR | 0.042 ±0.009 |
| PEEK AGAINST PACKED SALT WITH PRESSURE | 0.166 ± 0.034 |

FIG. 7B: *EXEMPLARY Wettability Data- Roughness*

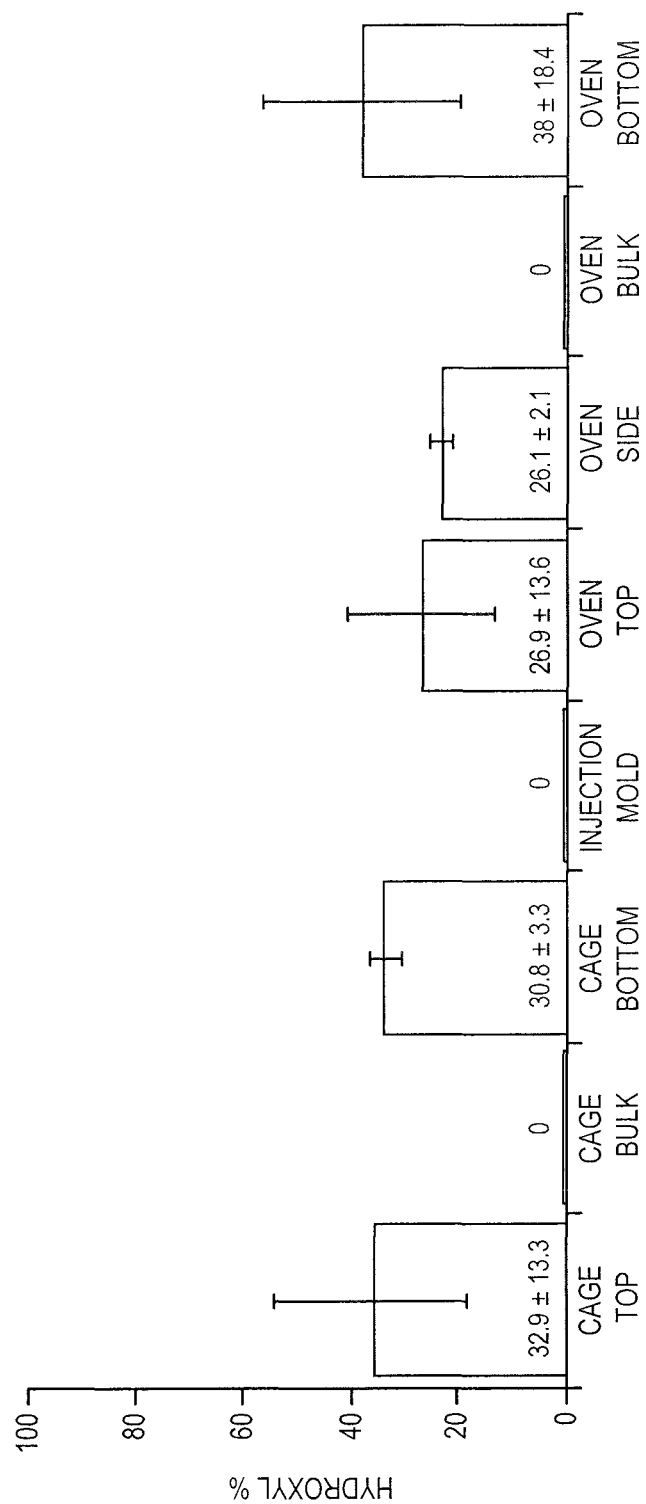
FIG. 8A: EXEMPLARY Hydroxyl Group Data- Processing Temperature

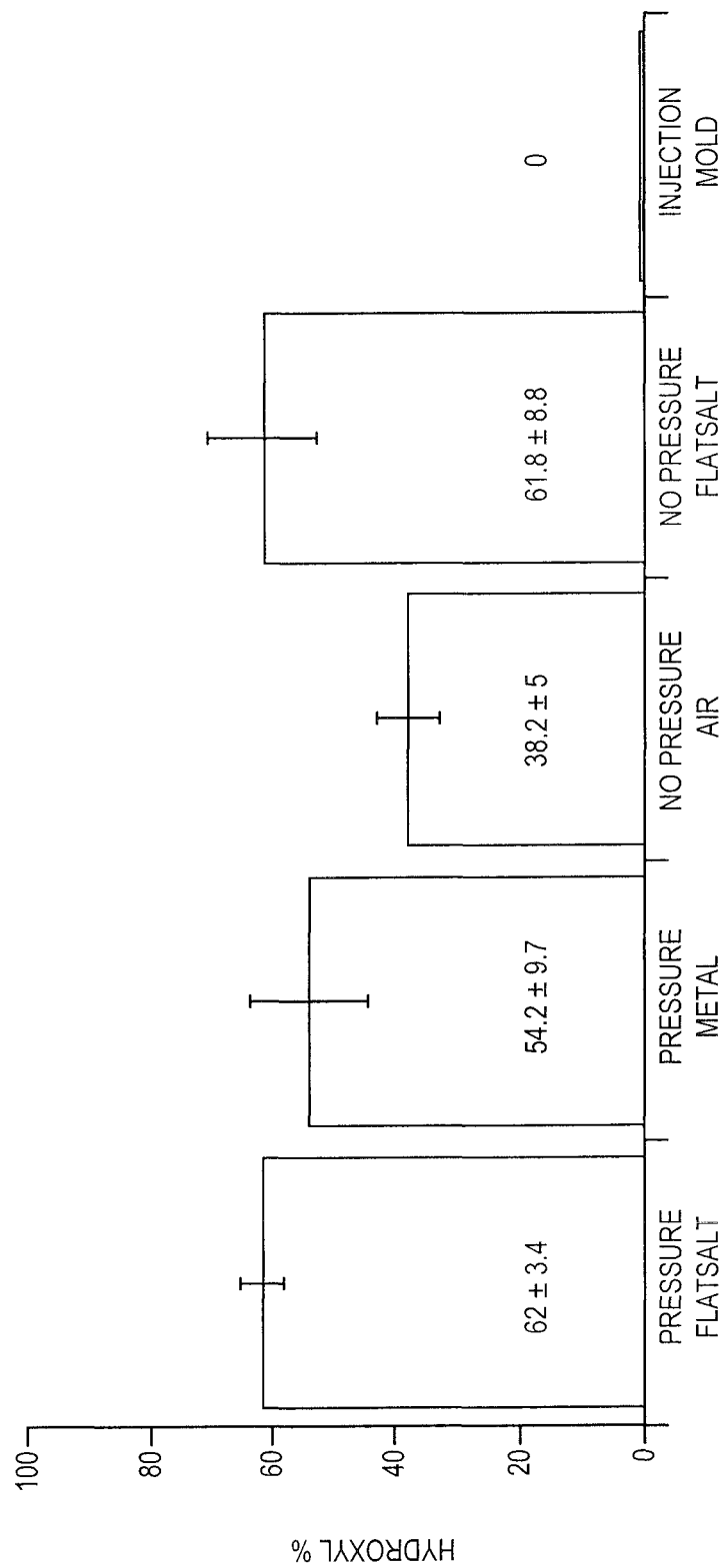
FIG. 8B: *EXEMPLARY Hydroxyl Group Data- Pressure*

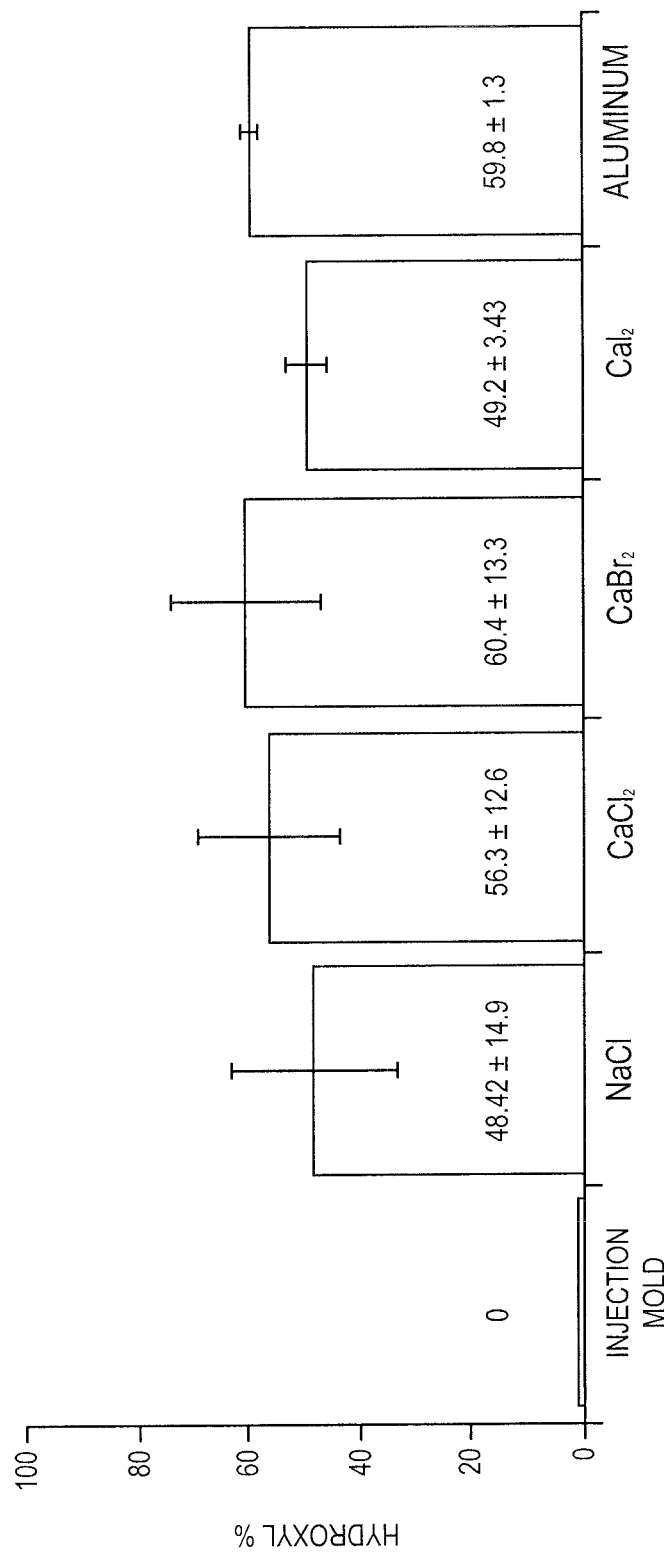
FIG. 8C: *EXEMPLARY Hydroxyl Group Data- Substrate*

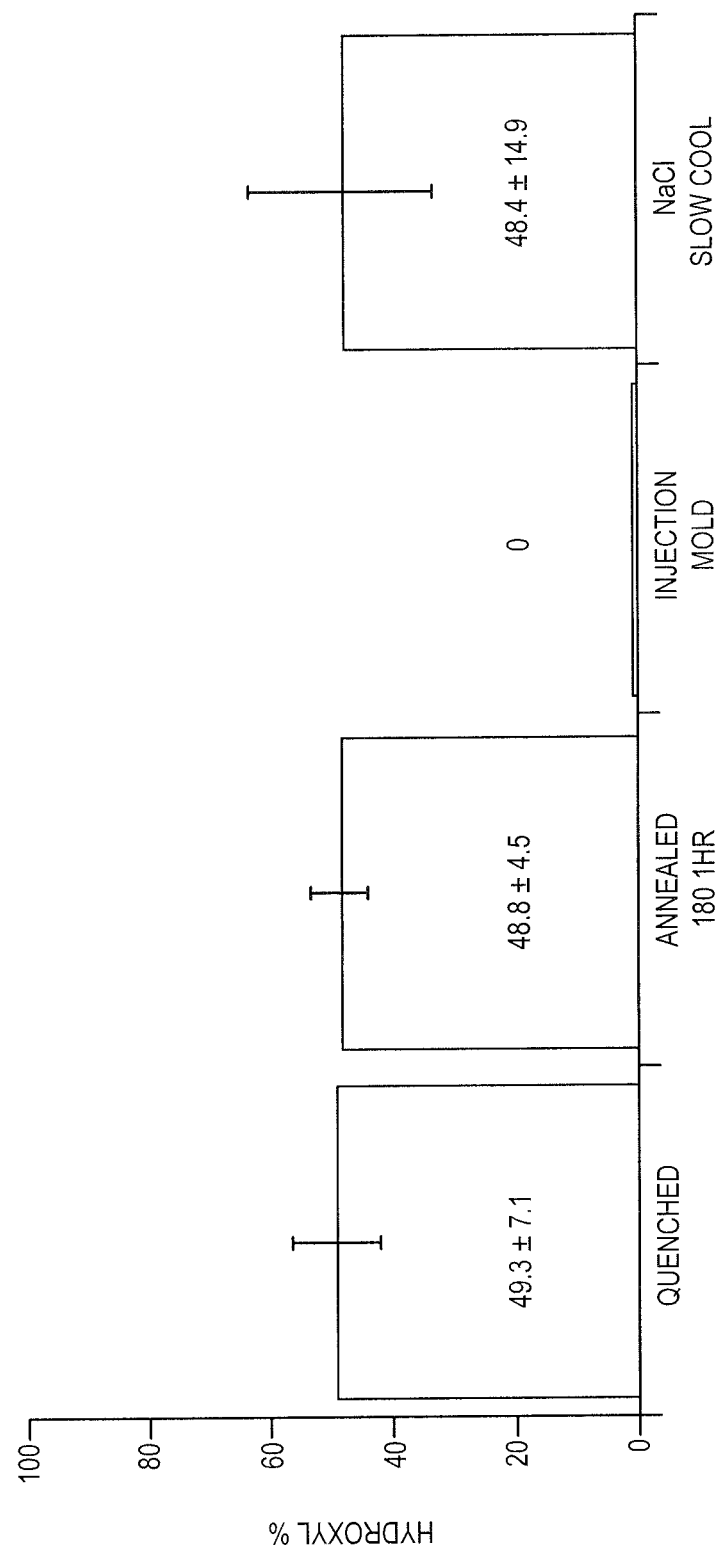
FIG. 8D: *EXEMPLARY Hydroxyl Group Data- Cooling Rate*

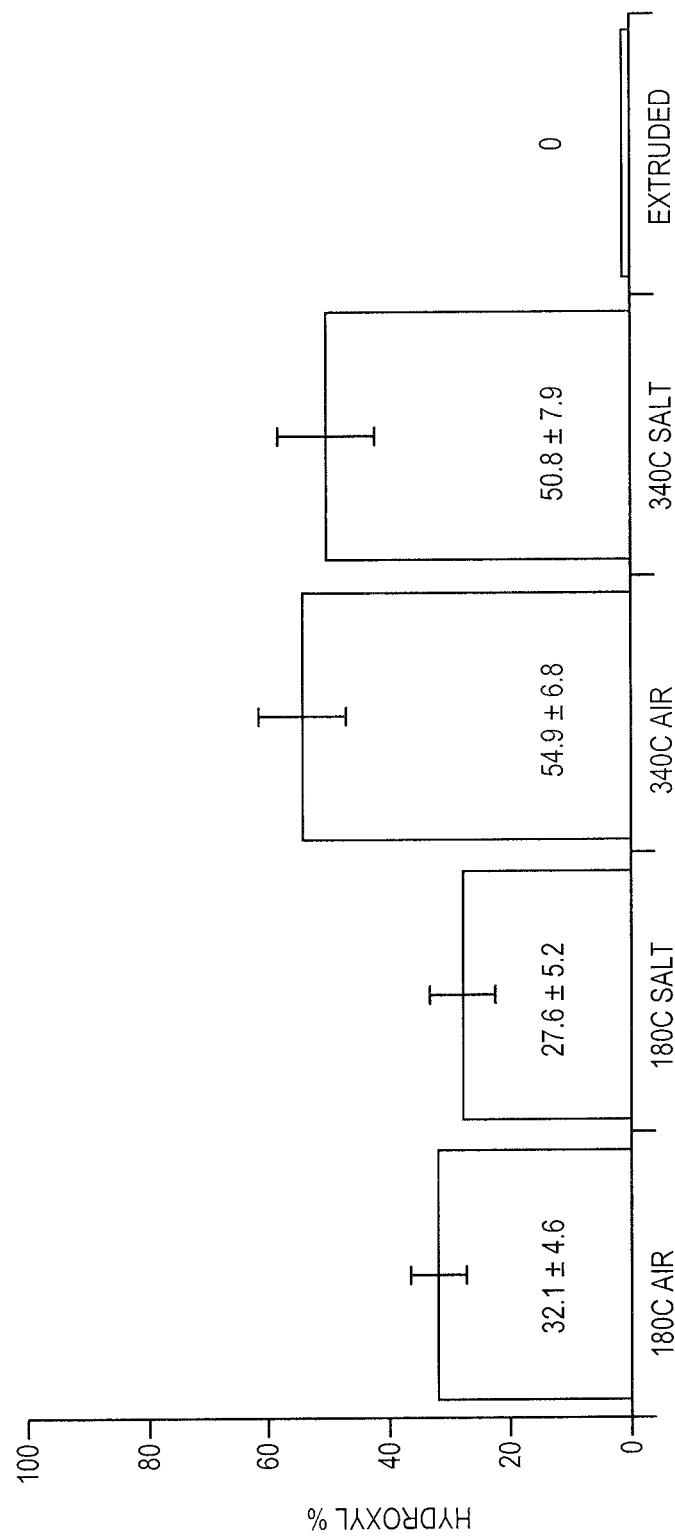
FIG. 8E: EXEMPLARY HYDROXYL GROUP DATA – VARYING TEMPERATURES

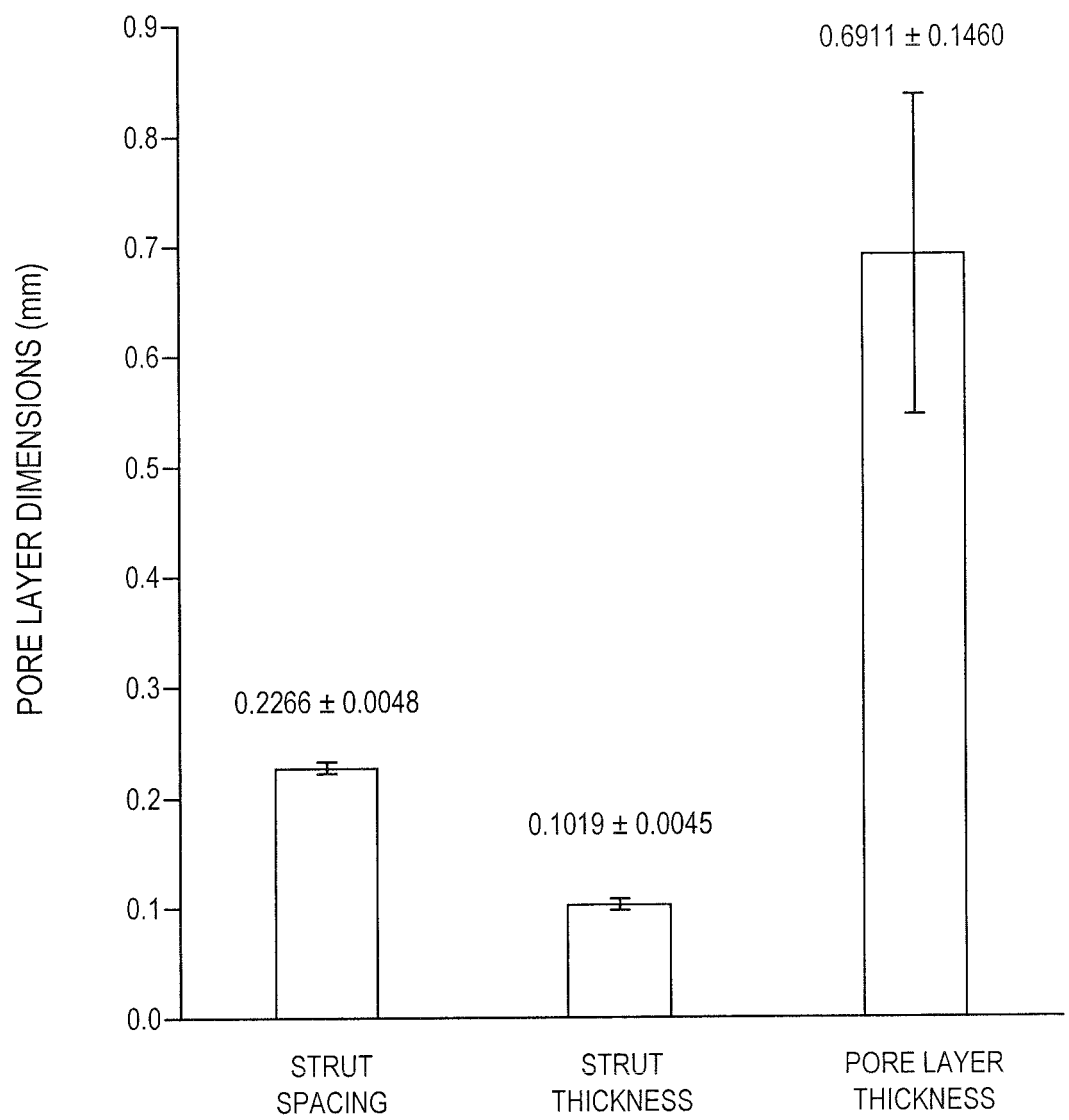
FIG. 9A: *EXEMPLARY Porous Layer Data*

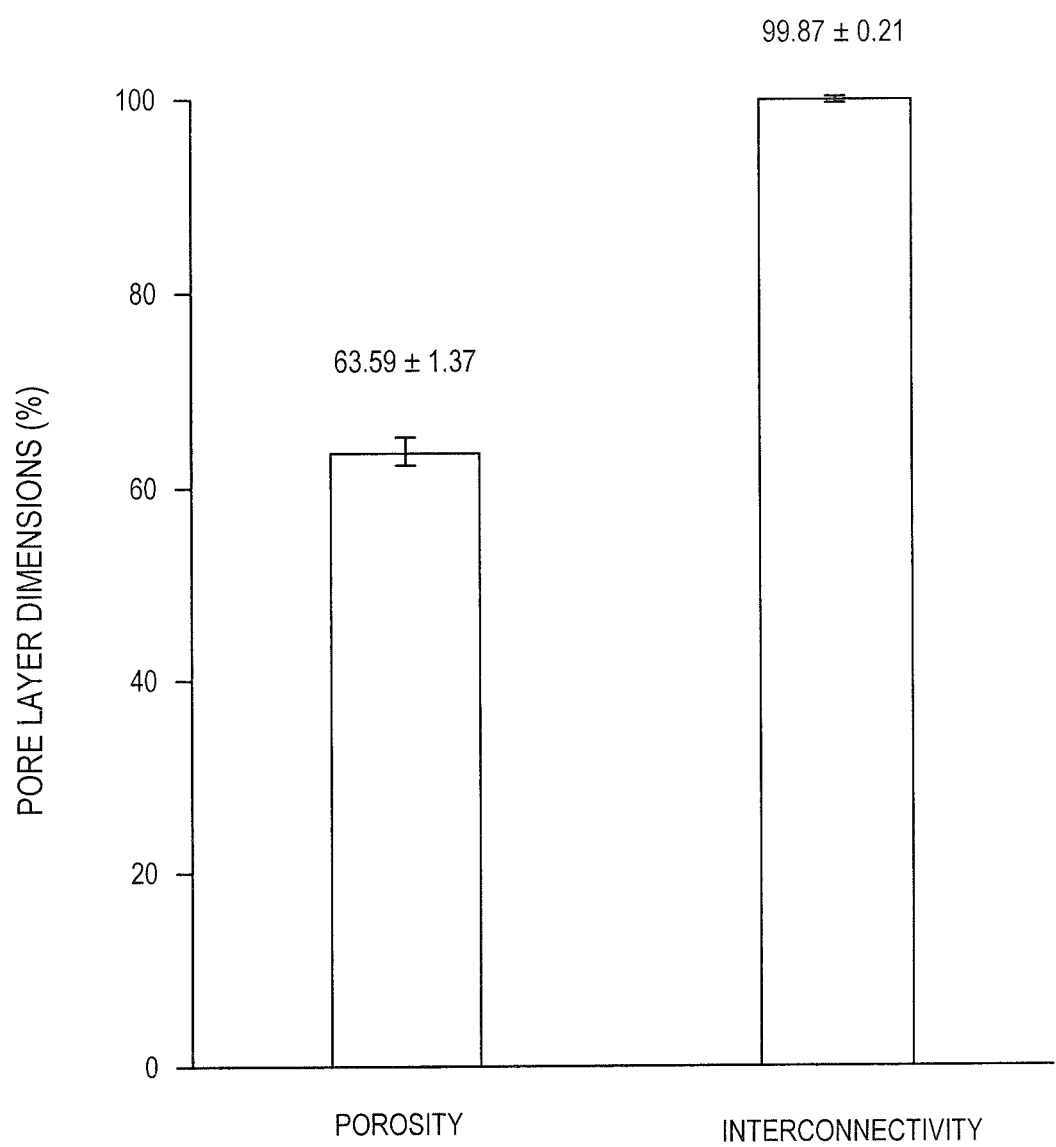
FIG. 9B: *EXEMPLARY Porous Layer Data*

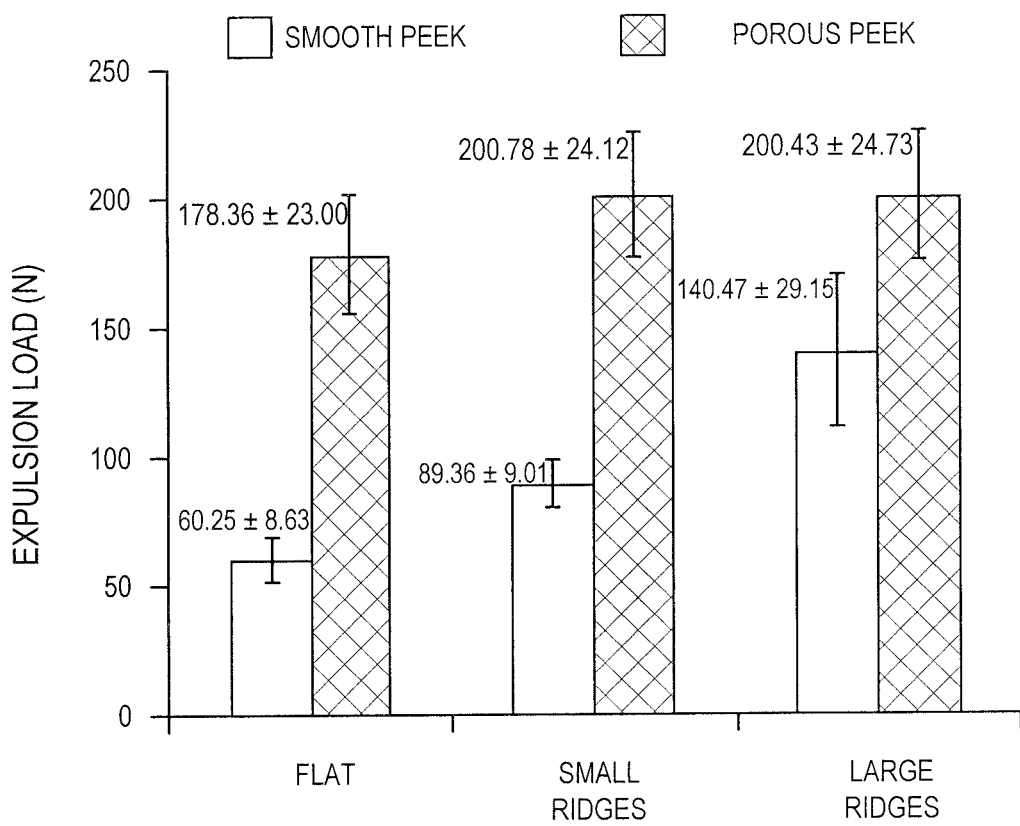
FIG. 10: EXEMPLARY Expulsion Force Data

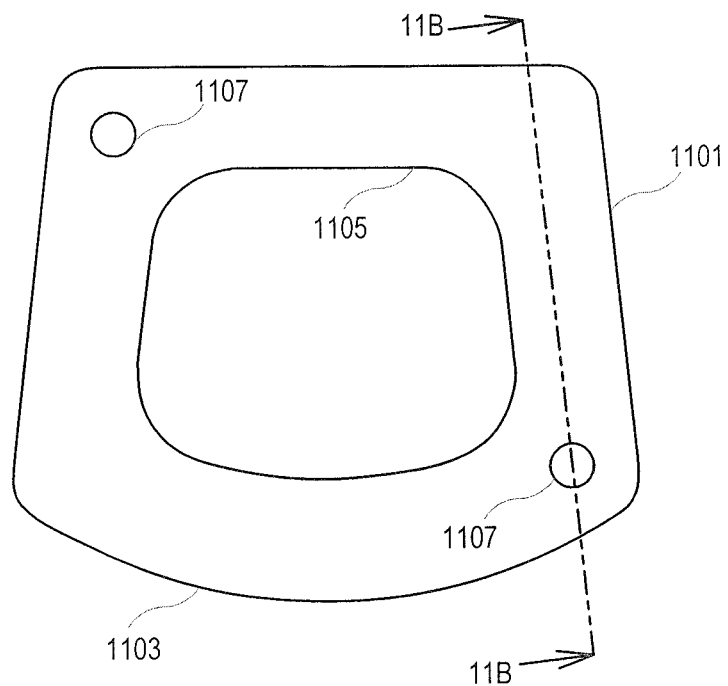
FIG. 11A: EXEMPLARY Medical Device
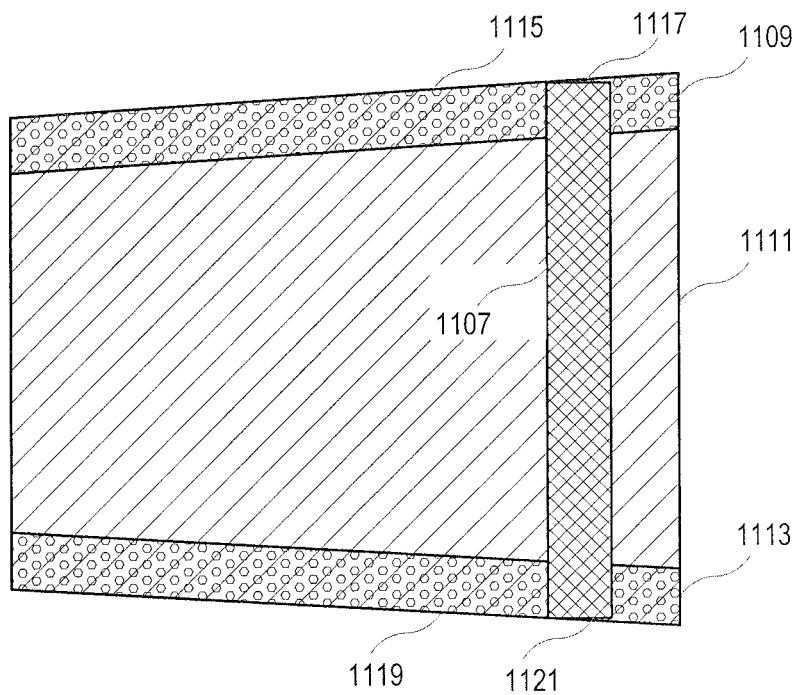
FIG. 11B: EXEMPLARY Medical Device

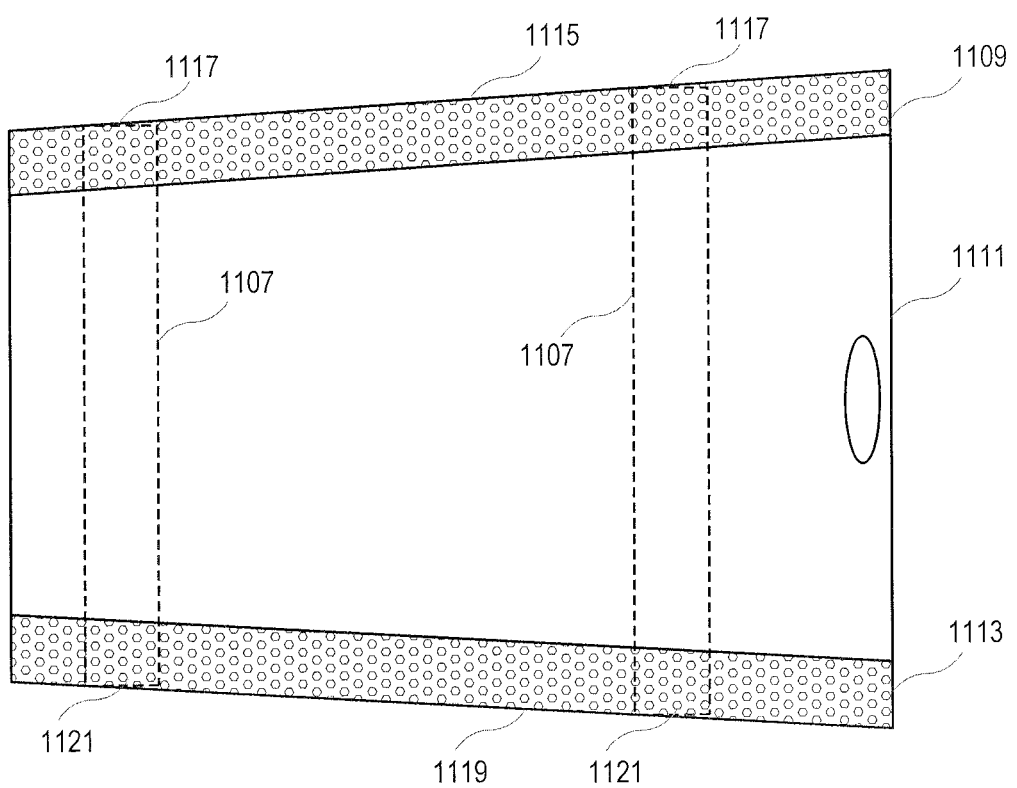
FIG. 11C: EXEMPLARY Medical Device

POROUS DEVICES AND PROCESSES FOR PRODUCING SAME

CROSS REFERENCE TO RELATED APPLICATIONS

The present application is a continuation of U.S. patent application Ser. No. 15/854,746, filed Dec. 26, 2017, which is a continuation of U.S. patent application Ser. No. 15/362,223, filed Nov. 28, 2016, which is a continuation of U.S. patent application Ser. No. 14/752,762, filed Jun. 26, 2015, entitled "Porous Devices and Processes for Producing Same", which:

is a continuation-in-part application of Ser. No. 14/587,856, filed Dec. 31, 2014, entitled "Method for Producing Porous Material", now U.S. Pat. No. 9,085,665; and claims the benefit under 35 U.S.C. sctn. 119 of, and priority to, U.S. Provisional Patent Application No. 62/017,834, filed Jun. 26, 2014, entitled, "Polymer Layer with Increased Wettability," each of which are incorporated herein by reference in their entireties.

This application incorporates by reference herein the following patent applications:

U.S. patent application Ser. No. 12/997,343, entitled "Material and Method for Producing the Same," filed on Jan. 19, 2011;

U.S. patent application Ser. No. 13/558,634, entitled "Porous Material and Method for Producing the Same," filed on Jul. 26, 2012;

U.S. patent application Ser. No. 12/997,343, entitled "Material and Method for Producing the Same," filed on Jan. 19, 2011;

International Patent Application (PCT) No. PCT/US2009/047286, entitled "Material and Method for Producing the Same," filed on Jun. 12, 2009;

International Patent Application (PCT) No. PCT/US2013/055656, entitled "Systems and Methods for Making Porous Films, Fibers, Spheres, and Other Articles," filed on Aug. 20, 2013; and International Patent Application (PCT) No. PCT/US2013/055655, entitled "Particulate Dispensing Apparatus," filed on Aug. 20, 2013.

TECHNICAL FIELD

The present disclosure relates generally to devices with porous surfaces and processes for creating porous polymers.

BACKGROUND

Polymers have been shown to have many advantageous mechanical and chemical properties such as imperviousness to water, low toxicity, chemical and heat resistance, and shape-memory properties. Additionally, polymers are often relatively low cost, easy to manufacture, and versatile in application. These characteristics have led to the use of polymers in many applications such as, for example, medical devices, electronics, optics, computing, and a wide-array of consumer products.

Adding pores to one or more surfaces of a polymer structure may provide further advantages, such as, for example, increasing friction at the one or more porous surfaces and providing better device integration in surgical applications by promoting adjacent tissue in-growth. However, as will be understood by one of ordinary skill in the art, introducing porosity into polymers may, in some instances, weaken desired mechanical properties, such as shear strength at the porous surface. Thus, although introducing pores into such polymers may have certain advantages, it has been limited in application due to a loss in mechanical properties.

BRIEF SUMMARY OF THE DISCLOSURE

One aspect of the present disclosure generally relates to producing a porous surface from a solid piece of polymer. In particular, producing a porous surface from a solid piece of polymer at a processing temperature below a melting point of the polymer to produce a solid piece of polymer with a porous surface integrated into the solid piece of polymer.

In a particular aspect, the present disclosure generally relates to producing a porous surface from a piece of polymer with shear strength that increases substantially linearly with processing time. In some aspects, the present disclosure relates to a method for forming a solid polymer body with pores distributed through at least a portion of the solid polymer body, the method comprising: A) heating a surface of a solid piece of polymer to a processing temperature below a melting point of the polymer; and B) holding the processing temperature while displacing a porogen layer through the surface of the polymer to create a matrix layer of the solid polymer body comprising the polymer and the porogen layer. This particular embodiment may further include a processing temperature that is about one to thirty-eight degrees Celsius less than the melting point of the polymer.

According to various aspects, the present disclosure relates to a method for forming a solid polymer body with pores distributed through at least a portion of the solid polymer body, the method including: A) placing a surface of a solid piece of polyetheretherketone (PEEK) in contact with a portion of a plurality of sodium chloride grain layers; B) heating the surface of the solid piece of PEEK to a processing temperature of about 305 to 342 degrees Celsius; C) holding the processing temperature of the surface of the solid piece of PEEK for a processing period of time of between about twenty and forty minutes to create a viscous layer of PEEK from the solid piece of PEEK; D) displacing at least the portion of the plurality of sodium chloride grain layers through the viscous layer of the solid piece of PEEK, creating a matrix layer of PEEK and sodium chloride grains; and E) leaching one or more of the chloride grains of the plurality of sodium chloride grain layers and cooling the surface of the solid piece of PEEK to form a solid polymer with a porous layer, wherein a shear strength of the porous layer increases substantially linearly with the processing period of time.

Particular aspects of the present disclosure relate to a method including: A) heating a surface of a solid polyetheretherketone (PEEK) body to a maximum processing temperature that is below a melting temperature of the surface of the solid PEEK body by a melting temperature differential; B) displacing a plurality of layers of a porogen through the surface and into a defined distance of the solid PEEK body, creating, thereby, a matrix layer including PEEK and the plurality of layers of the porogen, the matrix layer being integrally connected with the solid PEEK body; C) maintaining throughout the heating and displacing steps, a temperature of the surface of the solid PEEK body that is below the melting temperature by at least the melting temperature differential; and D) removing a portion of the plurality of layers of porogen from the matrix layer, creating, thereby, a porous PEEK layer integrally connected with a remaining portion of the solid PEEK body.

According to at least one aspect, a method, including: A) heating a surface of a solid polyetheretherketone (PEEK) body to a maximum processing temperature that is below a melting temperature of the surface of the solid PEEK body by a melting temperature differential; B) displacing a plurality of layers of a porogen through the surface and into a defined distance of the solid PEEK body, creating, thereby, a matrix layer including PEEK and the plurality of layers of the porogen, the matrix layer being integrally connected with the solid PEEK body; C) maintaining throughout the heating and displacing steps, a temperature of the surface of the solid PEEK body that is below the melting temperature by at least the melting temperature differential; and D) removing a portion of the plurality of layers of porogen from the matrix layer, creating, thereby, a porous PEEK layer integrally connected with a remaining portion of the solid PEEK body, wherein the temperature differential is between one degree Celsius and thirty-eight degrees Celsius.

According to some aspects, a method for forming a solid thermoplastic body with pores distributed through at least a portion of the solid, the method including: A) heating a surface of a solid piece of thermoplastic to a processing temperature below a melting point of the thermoplastic; B) holding the processing temperature below a melting point of the thermoplastic while displacing the surface of the thermoplastic through a granular porogen layer to create a matrix layer of the solid thermoplastic body including the thermoplastic and the porogen layer; and C) cooling the matrix layer to cease displacement of the granular porogen through the thermoplastic.

According to one or more aspects, a medical device for promoting tissue ingrowth, the medical device including a solid thermoplastic body including: A) a body layer, the body layer including a thermoplastic with crystallites varying in size; and B) a porous surface layer of the body, the porous surface layer of the body including irregular, substantially spherical pores extending through the solid thermoplastic body for a defined distance, wherein the interfacial shear strength between the body layer and the porous surface layer is at least about 17 MPa.

According to various aspects, a medical device for promoting tissue ingrowth, the medical device including a solid thermoplastic body including: A) at least two porous surface layers that are on opposite faces of the solid thermoplastic body, the at least two porous surface layers including irregular, substantially spherical pores extending through the solid thermoplastic body for a defined distance; and B) a body layer that is between the at least two porous surface layers, the body layer including a thermoplastic with crystallites varying in size, wherein: i) the at least two porous surface layers include an increased percentage of hydroxyl groups in comparison to the body layer; ii) a carbon to oxygen atomic ratio of the at least two porous surface layers is substantially the same as a carbon to oxygen atomic ratio of the body layer; iii) the at least two porous surface layers have increased wettability in comparison to the body layer; and iv) the interconnectivity of the irregular, substantially spherical pores is about 99%.

According to a particular aspect, a method, including: A) heating a surface of a solid polyetheretherketone (PEEK) body to a processing temperature that is above a glass transition temperature of PEEK; B) displacing a plurality of layers of a porogen through the surface and into a defined distance of the solid PEEK body; C) cooling the surface of the solid PEEK body at a predetermined rate; and D) removing a portion of the plurality of layers of porogen from the surface, creating, thereby, a porous PEEK layer integrally connected with a remaining portion of the solid PEEK body and including: i) an increased percentage of hydroxyl groups in comparison to a percentage of hydroxyl groups in the solid PEEK body; ii) a carbon to oxygen atomic ratio that is substantially the same as a carbon to oxygen atomic ratio of the solid PEEK body; and iii) an increased wettability in comparison to the solid PEEK body.

According to at least one aspect, medical device for promoting tissue ingrowth, the medical device including a thermoplastic body defining a porous surface formed from a plurality of substantially spherical pores, each of the pores extending a defined distance from the top face into the body, wherein: A) the porous surface has a particular wettability, wherein the particular wettability is greater than a wettability of the body; and B) an interconnectivity between the plurality of substantially spherical pores is at least 99%.

According to some aspects, a method for determining tissue ingrowth into a medical device, the method including: A) providing a medical device including: i) a radiolucent material; ii) a porous surface; and iii) at least one tantalum marker for detecting the medical device in a radiograph, wherein a top of the tantalum marker is approximately flush with a top of the porous surface; and B) instructing one or more clinicians to: i) take a radiograph of the medical device, wherein the medical device is implanted in a patient; and ii) measure the distance between the patient's tissue and the top of the at least one tantalum marker, thereby determining the tissue ingrowth of the patient's tissue into the medical device.

These and other aspects, features, and benefits of the claimed systems and methods will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

FIG. 1 is an exemplary flow chart of an exemplary process for creating a porous polymer, according to one embodiment.

FIG. 2 illustrates an exemplary process for creating a porous polymer, according to one embodiment.

FIG. 3 is an exemplary graph showing results of a differential scanning calorimetry scan of polyetheretherketone (PEEK) showing exemplary endotherms of PEEK under particular conditions, according to one embodiment.

FIG. 4A is an exemplary plot graph showing exemplary shear strength properties of PEEK over time under particular conditions, according to one embodiment.

FIG. 4B is an exemplary bar graph showing exemplary shear strength over time under particular conditions, according to one embodiment.

FIG. 4C is an exemplary plot graph showing exemplary pressure verses time data of PEEK under certain conditions, according to one embodiment.

FIG. 4D is an exemplary bar graph showing exemplary pressure verses time data of PEEK under certain conditions, according to one embodiment.

FIG. 5A is an exemplary plot graph showing exemplary shear strength properties of PEEK over time under particular conditions, according to one embodiment.

FIG. 5B is an exemplary bar graph showing exemplary shear strength properties of PEEK over time under particular conditions, according to one embodiment.

FIG. 5C is an exemplary plot graph showing exemplary pressure verses time data of PEEK under certain conditions, according to one embodiment.

FIG. 5D is an exemplary bar graph showing exemplary pressure verses time data of PEEK under certain conditions, according to one embodiment.

FIG. 6A is an exemplary XPS O1s spectra of an injection molded porous polymer under certain conditions, according to one embodiment.

FIG. 6B is an exemplary XPS O1s spectra of surface porous polymer under certain conditions, according to one embodiment.

FIG. 6C is an exemplary XPS O1s spectra of surface porous polymer after gamma sterilization under certain conditions, according to one embodiment.

FIG. 6D is an exemplary table comprising exemplary XPS O1s spectra ratios under certain conditions, according to one embodiment.

FIG. 6E is an exemplary table comprising exemplary XPS O1s elemental ratios under certain conditions, according to one embodiment.

FIG. 7A is an exemplary table comprising exemplary contact angles of a porous polymer under certain conditions, according to one embodiment.

FIG. 7B is an exemplary table comprising exemplary roughness data of a polymer under certain conditions, according to one embodiment.

FIG. 8A is an exemplary bar graph showing hydroxyl group percentages of a polymer verses processing temperature under certain conditions, according to one embodiment.

FIG. 8B is an exemplary bar graph showing hydroxyl group percentages of a polymer verses processing pressure under certain conditions, according to one embodiment.

FIG. 8C is an exemplary bar graph showing hydroxyl group percentages of a polymer verses processing substrate under certain conditions, according to one embodiment.

FIG. 8D is an exemplary bar graph showing hydroxyl group percentages of a polymer verses cooling rate under certain conditions, according to one embodiment.

FIG. 8E is an exemplary bar graph showing hydroxyl group percentages of a polymer verses processing temperature under certain conditions, according to one embodiment.

FIG. 9A is an exemplary bar graph showing exemplary porous layer dimensions of a polymer under certain conditions, according to one embodiment.

FIG. 9B is an exemplary bar graph showing exemplary porous layer properties of a polymer under certain conditions, according to one embodiment.

FIG. 10 is an exemplary bar graph showing exemplary expulsion load verses structure of a polymer under certain conditions, according to one embodiment.

FIG. 11A is a top view of a non-limiting, exemplary embodiment of a medical device, according to one embodiment.

FIG. 11B is a sectional view of a non-limiting, exemplary embodiment of a medical device, according to one embodiment.

FIG. 11C is a side view of a non-limiting, exemplary embodiment of a medical device, according to one embodiment.

DETAILED DESCRIPTION

Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended. Further, one or more references are incorporated by reference herein. Any incorporation by reference is not intended to give a definitive or limiting meaning of a particular term. In the case of a conflict of terms, this document governs.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Overview

According to particular embodiments, the systems and methods herein are directed to a process for producing a porous polymer including: 1) heating a surface of a solid piece of polymer to a processing temperature; 2) holding the processing temperature while displacing a porogen layer through the surface of the polymer to create a matrix layer of the solid polymer body including the polymer and the porogen layer; 3) cooling the surface of the polymer; and 4) removing at least a portion of the porogen layer from polymer. The processing temperature may be any suitable processing temperature, including a processing temperature below a melting point of the polymer. Further, as will be understood by one of ordinary skill in the art, different polymers may have different melting temperatures and some polymers may exhibit melting properties at more than one temperature.

Generally, this process results in a polymer with a porous surface layer on at least one surface of the polymer body. In various embodiments, the atomic ratio of carbon to oxygen in the porous surface layer is substantially the same as the atomic ratio of carbon to oxygen in the polymer body. In one or more embodiments, the porous surface layer has an increased percentage of hydroxyl groups in comparison to the polymer body. Accordingly, in one embodiment, the process is not be an addition reaction but instead is a reduction of a carbonyl and/or ether group to a hydroxyl group.

In one or more embodiments, the increased percentage of hydroxyl groups in the porous surface layer results in a more hydrophilic surface in comparison to unprocessed, smooth polymer. Thus, in various embodiments, the wettability of the porous surface layer is greater than the wettability of the unprocessed polymer body.

This process may also result in interfacial shear strength between the porous layer and solid polymer body that increases with longer processing times that are above a predetermined processing temperature (Tp), but below a melting point of the polymer. Further, pressure applied to exert polymer flow at a constant rate is significantly correlated statistically (i.e. p-value less than 0.05 as calculated by linear regression analysis) with processing time above a defined processing temperature of 330 degrees Celsius for up to 30 to 45 minutes. This correlation is counter to expected results and indicates that polymer flow viscosity increases with increased processing time below PEEK's melting point of 343 degrees Celsius (e.g., increased processing time at about one to 13 degrees below 343 degrees Celsius, or between about 330 and 342 degrees Celsius).

As a particular example, it has been shown that PEEK increases in viscosity over time for particular processing temperatures. Continuing with this particular example, a sample of PEEK that is heated to a processing temperature of about 340 degrees Celsius has a viscosity of about 47,000 Pa*s at zero seconds, but increases to about 106,000 Pa*s at about 1800 seconds if this processing temperature is held substantially constant. Similarly, continuing with this example, a sample of PEEK that is heated to a processing temperature of about 360 degrees Celsius has a viscosity of about 2,600 Pa*s at zero seconds, but increases to about 3,200 Pa*s at about 1800 seconds if this processing temperature is held substantially constant.

The porous surface layer may include any suitable features based on its intended application. For example, the porous surface layer, in various embodiments, may be between about 0.55 mm and 0.85 mm thick. In a particular embodiment, the porous surface layer may be approximately 0.7 mm thick. Similarly, the struts, which define the shape of the pores in the porous surface layer, may be spaced between about 0.21 mm and 0.23 mm apart with a thickness of between about 0.9 mm and 0.11 mm. Throughout the porous surface layer, in a particular embodiment, the porosity is between about 61% and 66% and the interconnectivity of the pores may be about 99%.

The above-described process may be used to create a spinal implant of substantially cubic shape with a porous layer on the top and bottom surfaces with any of the exemplary physical or chemical properties discussed above. Generally, the spinal implant may, because of the wettability of the porous layers, promote adhesion of proteins that then promote tissue ingrowth. Further, the spinal implant may, because of the topographical features of the porous layer, promote tissue ingrowth. Moreover, cylindrical markers may be inserted into the spinal implant so that the amount of tissue ingrowth may be visualized using standard electromagnetic-imaging techniques.

As will be understood by one of ordinary skill in the art, "polymer flow" or "polymer flow viscosity", as used herein may refer to any flow of a particular polymer and may not necessarily mean flow of a polymer above a melting point of the particular polymer (although, in some embodiments, polymer flow, as discussed herein, may refer to flow of a particular polymer above a melting point of the particular polymer). In specific embodiments, "polymer flow" and "polymer flow viscosity" refer to flow of a polymer below a melting point of the polymer. Alternately, polymer flow or polymer flow viscosity may be referred to as "polymer resistance to displacement" or the like.

As will be understood by one of ordinary skill in the art, any suitable materials may be used in the above process or in the above-described devices. In at least one embodiment, the polymer in the above exemplary process is polyetheretherketone (PEEK). In one or more embodiments, the porogen in the above exemplary process is sodium chloride grains arranged in one or more layers, such that when the polymer is heated it at least partially flows between the gaps of the layers of the sodium chloride particles.

Exemplary Process

Turning now to FIG. 1, an exemplary process for producing a porous polymer is shown. This exemplary process begins at step 110 by heating a surface of a solid piece of polymer to a processing temperature below a melting point of the polymer. In various embodiments, the surface is heated in any suitable way, such as by conductive heating, microwave heating, infrared heating, or any other suitable heating method.

Any surface of the solid piece of polymer may be heated. In a particular embodiment shown in FIG. 2, a bottom surface is placed in contact with a porogen layer and heated such that the porogen layer is at least partially displaced within the bottom surface. In various embodiments, a top or side surface is placed in contact with a porogen layer and/or heated such that the porogen layer is at least partially displaced within the top or side surface. As will be understood by one of ordinary skill in the art, a "surface" of the solid piece of polymer may be any suitable portion (or all surfaces) of the solid piece of polymer and, in at least one embodiment, is the entire piece of polymer.

The solid piece of polymer may be any suitable material. In a particular embodiment, the polymer is polyetheretherketone (PEEK). In various embodiments, the polymer is any other suitable thermoplastic with similar properties as PEEK, such as any polymer with multiple endotherms and/or broad endotherms and/or any polymer that exhibits flow above the glass transition. The polymer may be, for example, carbon fiber reinforced PEEK, polymethylmethacrylate (PMMA), polycarbonate (PC), polyphenylsulfone (PPSU), polyphenylenesulfide (PPS), polyethersulfone (PES), polyparaphenylene (also known as self-reinforcing polyphenylene or SRP), or thermoplastic polyurethane (TPU).

The processing temperature may be any suitable temperature and may depend upon the melting point for the particular polymer. In a particular embodiment, the polymer is PEEK, with a melting point of about 343 degrees Celsius. In these embodiments (and others), the processing temperature may be any suitable range below the melting point of PEEK (e.g., 343 degrees Celsius). In one or more embodiments, as discussed below, the processing temperature is about one (1) to 38 degrees below the melting point of PEEK (e.g., the processing temperature is approximately 305 to 342 degrees Celsius). In at least one embodiment, the processing temperature is about 330 degrees Celsius for PEEK. In another embodiment, the processing temperature is about 340 degrees Celsius for PEEK. As will be understood by one of ordinary skill in the art, the processing temperature, in particular embodiments, is the processing temperature of the polymer surface.

At step 120, the process continues with holding the processing temperature while displacing a porogen layer through the surface of the polymer to create a matrix layer of the solid polymer body including the polymer and the porogen layer. In various embodiments, the porogen layer includes particles of one or more particular materials such as sodium chloride grains or other salts, sugars, polymers, metals, etc.

The particles of the porogen layer may be arranged in any suitable way. In various embodiments, the particles of the porogen layer are arranged in a regular lattice pattern, with each particle touching at least one other particle. In some embodiments, the particles of the porogen layer are arranged in an irregular geometric pattern and/or are packet down without a planned geometric pattern.

Further, the particles of the porogen layer may be of any suitable size and shape. In particular embodiments, the particles of the porogen layer may be pre-processed such that they are one or more specific shapes, such as substantially spherical, substantially cubic, etc. In at least one embodiment the particles of the porogen layer are packed, irregular grains of a salt.

In various embodiments, the porogen layer is displaced through the surface of the polymer by holding the processing temperature by applying pressure to the polymer to force the polymer (which may be viscous from heating, as discussed herein) through gaps between the porogen layer (e.g., the porogen is packed and arranged such that there are gaps between the particles). In at least one embodiment, the result is a matrix layer with polymer in gaps between the particles of the porogen layer.

In embodiments where the porogen layer is located at a side surface or more than one surface of the piece of polymer, pressure may be applied in one or more directions to the solid piece of polymer. In one or more such embodiments, pressure may be applied to all sides of the solid piece of polymer (e.g., to create a structure with more than one porous surface).

The porogen layer may be displaced through the surface of the polymer to any suitable depth. In a particular embodiment, the porogen layer is displaced through the surface of the polymer to a depth of approximately 0.2 mm to 2.0 mm.

At step 130, the process continues with removing at least a portion of the porogen layer from the matrix layer to form a solid polymer with a porous layer. As will be understood by one of ordinary skill in the art, the portion of the porogen layer to be removed may be removed in any suitable way and the method of removal may be dependent upon the composition of the porogen layer. Exemplary methods of removing all or a portion of the porogen layer include (but are not limited to): leaching, washing, etching, vaporizing, volatilizing, etc. For example, in embodiments where the porogen layer includes sodium chloride grains, some or all of the sodium chloride grains may be removed by leaching (e.g., dissolving all or a portion of the porogen layer with a particular solvent).

As will be understood by one of ordinary skill in the art, any portion of the porogen layer may be removed. In various embodiments, the desired final product may include a solid polymer portion, a matrix layer, and a porous layer. In these embodiments, only a portion of the porous layer may be removed (e.g., to a certain depth), leaving a structure including a solid polymer layer, a matrix layer (including the polymer and porogen) and a porous polymer layer. In some embodiments, the desired structure does not include any of the porogen layer and substantially all of the porogen layer is removed, resulting in a structure that includes a solid polymer and a porous polymer layer. In embodiments where the matrix layer is the desired outcome, this step 130 may be omitted.

FIG. 2 depicts an exemplary process for producing a porous polymer under certain conditions. In particular, FIG. 2 shows a polymer sample placed in contact with a packed array of porogen (sodium chloride) grains at step 1. In this particular example, the porogen grains are arranged at a depth of approximately 0.2 to 2 mm. In various embodiments, the arrangement of porogen grains affects the arrangement of pores in a resulting porous layer of the polymer sample and thus, the depth may be any suitable depth depending on the desired depth of pores or of a resulting matrix layer. For example, porogen grains may be arranged at depths of approximately 0.05 mm to 5 mm or any suitable range in between.

Continuing with step 1, the surface of the polymer in contact with the porogen grains is heated to a particular processing temperature under an initial pressure of about 2 PSI. In various embodiments, the particular processing temperature is below a melting point of the polymer. For example, as discussed below, PEEK exhibits melting temperatures at approximately 240 and 343 degrees Celsius.

As will be understood by one of ordinary skill in the art, the initial pressure may be any suitable initial pressure. In various embodiments, the initial pressure is about 0.1 to 10 PSI. In some embodiments, the initial pressure and the final pressure are the same (e.g., the same pressure is held constant throughout the entire process).

At step 2, once the polymer surface is heated to the processing temperature, additional pressure is applied to the polymer. In particular embodiments, the processing temperature and the additional pressure is held for a predetermined processing time and, as shown in step 3, the porogen is displaced within the surface of the polymer, creating a pore network (e.g., under particular conditions, the polymer flows between the porogen). According to various embodiments, the processing time is for about zero (0) to 45 minutes. In one embodiment, the processing time is for about 30 minutes.

The additional pressure may be any suitable pressure. In particular embodiments the additional pressure is up to 250 PSI. In one or more embodiments, the additional pressure is between 50 and 250 PSI. In at least one embodiment, the additional pressure is about 150 PSI.

At step 4, the additional pressure and heat are removed from the polymer and the polymer surface is cooled in a controlled fashion to manage solidification and crystallization. At step 5, the porogen grains are leached, leaving behind a thin porous surface layer that is integrally connected with the solid polymer body. Precise control of local temperature, pressure, and time may achieve desired pore layer characteristics. As will be understood by one of ordinary skill in the art, as shown in step 6, the introduction of surface porosity may result in expansion of the total polymer structure, indicated by the change in height, .DELTA.h.

Exemplary PEEK Data

As will be further discussed herein, PEEK exhibits melting properties at two temperatures under particular conditions. As shown in FIG. 3, PEEK exhibits several thermal transitions in this differential scanning calorimetry (DSC) scan. The first (lowest temperature) transition is the glass transition, which is characterized by a shift in the heat capacity of the polymer. As shown, this glass transition occurs at approximately 145 degrees Celsius.

Continuing with FIG. 3, PEEK displays higher temperature transitions, characteristic of melting (e.g., endotherms). As will be understood by one of ordinary skill the art, the enthalpy of melting, the increased heat energy required to overcome the crystalline order, is shown by the area of the endotherm. Notably, in the embodiment shown in FIG. 3, PEEK shows a double melting behavior under these conditions with a small (lower temperature) endotherm and a large (higher temperature) endotherm. As shown, the first endotherm is measured at approximately 240 degrees Celsius and the second endotherm is measured at approximately 343 degrees Celsius. This "double peak" behavior has been explained as a two-stage melting process occurring due to varying size crystallites. However, it should be noted that melting occurs over a range of temperatures and the melting temperature (Tm) is generally determined from the temperature corresponding to the peak maximum of the second melting endotherm (e.g., 343 degrees Celsius, shown here). It should also be noted that endotherms for samples of a polymer may vary based on crystallinity of the polymer;

thus, samples of the same polymer may have slightly varying endotherms based on slightly different crystalline structures (e.g., one PEEK sample may have a first endotherm at 239.5 degrees Celsius and a second PEEK sample may have a first endotherm at 241 degrees Celsius).

Exemplary Shear Strength Data

FIGS. 4A and 4B, show exemplary shear strength for PEEK measured over processing times of zero (0) to 30 minutes. As shown in FIGS. 4A and 4B, resulting interfacial shear strength between the porous layer and solid polymer body increases with longer processing times above a predetermined processing temperature (Tp). In particular, FIGS. 4A and 4B show that shear strength between the porous layer and solid polymer body increases substantially linearly with increased processing times between zero (0) and 30 minutes at temperatures of Tp. Tp in this instance is 330 degrees Celsius, which, as depicted in FIG. 3 and discussed above, is below the 343 degrees Celsius melting point of PEEK.

FIGS. 5A and 5B show exemplary shear strength for PEEK measured over processing times of about zero (0) to 40 minutes. As shown in FIGS. 5A and 5B, the shear strength of PEEK potentially begins to plateau between a processing time of around 30 to 40 minutes. Particularly, the shear strength of PEEK is significantly correlated statistically (i.e. p-value less than 0.05 as calculated by linear regression analysis) with processing time above a defined processing temperature of about 330 degrees Celsius (which is thirteen degrees lower than the melting temperature for PEEK of 343 degrees Celsius) for up to about 30 to 45 minutes.

Exemplary Pressure Data

FIGS. 4C and 4D show pressure data verses time above processing temperature (Tp), while holding a constant polymer flow rate (as discussed herein, polymer flow may refer to polymer flow below a melting temperature of the polymer). The polymer flow rate may be any suitable rate, such as approximately two (2) mm/minute. As will be understood by one of ordinary skill in the art, FIGS. 4C and 4D (and 5C and 5D) depict pressures trending in a negative direction, which indicates an increase in pressure acting in compression. It should be understood that an increase in pressure may be shown as positive or negative.

FIGS. 4C and 4D provide a potential explanation for the substantially linear increase in shear strength with increased processing time above a specified processing temperature as shown in FIGS. 4A and 4B (about 330 degrees Celsius in this instance, which is below the 343 degrees Celsius melting temperature of PEEK). In particular, the increased shear strength may be due to an increase in polymer flow viscosity. As will be understood by one of ordinary skill in the art, polymer flow viscosity typically decreases or remains constant as it is heated for longer periods of time. However, as shown in FIGS. 4C and 4D, pressure applied to exert polymer flow at a constant rate is significantly correlated statistically (i.e. p-value less than 0.05 as calculated by linear regression analysis) with processing time above a defined processing temperature of about 330 degrees Celsius for up to 30 to 45 minutes. This correlation is counter to expected results and indicates that polymer flow viscosity increases with processing time below 343 degrees Celsius. This phenomenon appears to plateau around 30 to 45 minutes as shown in FIGS. 5C and 5D.

As will be understood by one of ordinary skill in the art, FIGS. 4C, 4D, 5C, and 5D show data based on holding a constant rate of polymer flow (e.g., polymer flow is held constant and pressure applied to hold the polymer flow constant over time is measured), but this process may operate in the reverse. In various embodiments, pressure is known and applied linearly to keep polymer flow constant.

Exemplary Wettability Data

As shown and described herein, in various embodiments, wettability via hydroxyl/carboxyl group % increases at the surface is shown to be independently controllable independent of substrate or porogen type and pressure applied to the interface. This potentially contradicts earlier work claiming dependence on surface energy of the substrate surface. To the contrary, shown herein are increases in hydroxyl % and wettability thereby that is independent of surface energetics of the substrate or pressures applied, and instead is heavily dependent on a controlled heating and cooling rate of the infiltrating and recrystallizing PEEK.

FIGS. 6A, 6B, and 6C show XPS O1s spectra of a polymer in an unprocessed state and processed in various ways, including at least substantially processed in accordance with the processes described herein. In a particular embodiment, as shown in FIG. 6A, unprocessed polymers (e.g., PEEK) exhibit a peak at 535 to 530 eV. Generally, this peek may be explained by the presence of the carbon to oxygen single and double bonds as would be expected in PEEK (e.g., with ether and ketone groups, respectively), with more carbon to oxygen single bonds present than double bonds. In a particular embodiment, as shown in FIG. 6B, the porous surface of processed polymers (e.g., PEEK) exhibit a different peak at 535 to 530 eV, with a noticeable shift to lower binding energy. Generally, this peek may be explained by the presence of oxygen to hydrogen single bonds (e.g., hydroxyl groups) in addition to the carbon to oxygen single and double bonds as would be expected in PEEK, with the concentration of oxygen to hydrogen single bonds between that of the carbon to oxygen single and double bonds. In a particular embodiment, as shown in FIG. 6C, the porous surface of processed polymers after gamma sterilization (e.g., PEEK) also exhibit a different peak at 535 to 530 eV, with a noticeable shift to lower binding energy. Generally, this peek may be explained by the presence of oxygen to hydrogen single bonds in addition to the carbon to oxygen single and double bonds as would be expected in PEEK, with the concentration of hydroxyl groups exceeding that of the carbon to oxygen single and double bonds.

FIGS. 6D and 6E show tables with atomic and molecular percentages from the XPS O1s spectra of a polymer in an unprocessed state and processed in various ways, including at least substantially processed in accordance with the processes described herein. In various embodiments, the carbon to oxygen atomic ratio does not change in processed polymers, but there is an increased percentage of hydroxyl groups after processing.

In various embodiments, as shown in FIG. 6D, the unprocessed polymers (e.g., injection molded and extruded PEEK) comprise approximately 0% hydroxyl groups, 70% ether groups, and 30% ketone groups. In a particular embodiment, the injection molded PEEK comprises 65.65% ether groups and 34.34% ketone groups but may comprise 60-70% ether groups and 30-40% ketone groups. Similarly, in a particular embodiment, the extruded PEEK comprises 70.06% ether groups and 29.93% ketone groups but may comprise 65-75% ether groups and 35-45% ketone groups.

In various embodiments, as shown in FIG. 6D, the processed polymers (e.g., porous PEEK and porous PEEK after gamma sterilization) comprise approximately 50% hydroxyl groups, 30% ether groups, and 20% ketone groups. In a particular embodiment, the porous PEEK comprises 48.42% hydroxyl groups, 31.48% ether groups, and 20.09% ketone groups but may comprise 40-60% hydroxyl groups, 20-40% ether groups, and 10-30% ketone groups. Similarly, in a particular embodiment, the porous PEEK after gamma sterilization comprises 50.50% hydroxyl groups, 28.95% ether groups, and 20.53% ketone groups but may comprise 45-55% hydroxyl groups, 25-35% ether groups, and 15-25% ketone groups.

In various embodiments, as shown in FIG. 6E, the unprocessed (e.g., injection molded and extruded PEEK) and processed polymers (e.g., porous PEEK and porous PEEK after gamma sterilization) comprise similar carbon to oxygen atomic ratios (e.g., carbon to oxygen atomic ratio of 3.3 for the processed polymers and 3.4 for the unprocessed polymers). In a particular embodiment, the injection molded PEEK comprises 79.97% carbon atoms and 20.02% oxygen atoms but may comprise 75-85% carbon atoms and 15-25% oxygen atoms. Similarly, in a particular embodiment, the extruded PEEK comprises 84.39% carbon atoms and 15.6% oxygen atoms but may comprise 80-90% carbon atoms and 10-20% oxygen atoms. In a particular embodiment, the porous PEEK comprises 79.82% carbon atoms and 20.18% oxygen atoms but may comprise 75-85% carbon atoms and 15-22% oxygen atoms. Similarly, in a particular embodiment, the porous PEEK after gamma sterilization comprises 84.17% carbon atoms and 15.83% oxygen atoms but may comprise 80-90% carbon atoms and 10-20% oxygen atoms.

FIG. 7A shows exemplary wettability data of a polymer in an unprocessed state and processed in various ways, including at least substantially processed in accordance with the processes described herein. As will be understood by one of ordinary skill in the art, a decrease in the contact angle of a fluid (e.g., water) on the surface of a solid (e.g., PEEK) indicates an increase in the wettability of the solid. As shown in FIG. 7A, the wettability of unprocessed PEEK is relatively low, with a contact angle of at least 70 degrees. Further, as also shown in FIG. 7, the wettability of PEEK that has only been thermally treated and did not come into contact with a salt porogen is also relatively low, with a contact angle of at least 70 degrees. Continuing with FIG. 7, the wettability of PEEK that came into contact with a salt porogen (with or without pressure) is relatively high, with a contact angle below 52 degrees. In a particular embodiment, the wettability of PEEK that came into contact with a packed salt porogen with pressure is also relatively high, with a contact angle below 27 degrees. The wettability of a porous polymer produced in accordance with the processes described herein (e.g., "Surface Porous PEEK Cage" in FIG. 7A) is very high, with a contact angle of about 0 degrees.

FIG. 7B shows exemplary roughness data of salt crystals and a polymer after various processing. As will be understood by one of ordinary skill in the art, a fluid may wick into pores of a porous surface. Thus, the roughness of a surface may be thought to be the primary contributor to wettability. As shown in FIG. 7B, the roughness for an extruded polymer ("EXTRUDED PEEK"), a polymer pressed against a single crystal salt ("PEEK THERMALLY TREATED 340 C AGAINST SINGLE CRYSTAL SALT"), and a polymer thermally treated without salt ("PEEK THERMALLY TREATED 340 C AIR") are similar. Further, the roughness of salt crystals ("SALT CRYSTALS") is similar to that of a polymer pressed against pack salt with pressure ("PEEK AGAINST PACKED SALT WITH PRESSURE"). The roughness for a polymer substantially processed in ways described herein, as shown in FIG. 7B as "SURFACE POROUS PEEK CAGE", has a higher roughness than the other samples shown.

After processing as described herein, surface porous polymers, in various embodiments, have average roughness values greater than that of the porogen, salt crystals likely because the height/depth of the pore wall may increase the roughness (e.g., the roughness of SURFACE POROUS PEEK CAGE is greater than the other samples). Further, according to particular embodiments, macroscopically flat samples, either PEEK sheet pressed against packed flat salt or PEEK sheet pressed against single crystal salt, show roughness values similar to that of salt crystals and exhibit lower contact angles. As shown in FIG. 7B, extruded PEEK and PEEK thermally treated without salt have similar roughness values and exhibit similar contact angle values.

However, as shown in FIG. 7A, the contact angle for a polymer substantially processed in ways described herein ("SURFACE POROUS PEEK CAGE") has a much lower contact angle (e.g., about zero degrees). This suggests that the lower contact angle of the polymer substantially processed in ways described herein, and therefore with increased wettability, may be due to changes in composition of the porous polymers (e.g., chemical changes of the surface of the polymer) and an increased roughness of the surface (e.g., physical changes of the surface), opposed to an increase in roughness due only a physical change.

Exemplary Hydroxyl Group Data

FIGS. 8A, 8B, 8C, 8D, 8E show exemplary hydroxyl group data of an exemplary porous polymer (e.g., PEEK) produced in accordance with the processes described herein. As discussed herein, increased hydroxyl/carboxyl % may indicate increased wettability. Further, as discussed herein, heat treatment appears to be the main factor in the increase of hydroxyl %, and therefore, wettability. Specifically, in one embodiment, the heating of the polymer to the processing temperatures discussed herein results in an increased percentage of hydroxyl groups in the porous surface of the polymer in comparison to the body of the polymer or an unprocessed polymer.

FIG. 8A depicts a bar graph comparing hydroxyl group % of porous polymer heated in various ways. In the embodiment shown in FIG. 8A, surfaces that were heated to a temperature just below (e.g., approximately 340 degrees Celsius), at, or above about 343 Celsius (e.g., a melting temperature of PEEK), flowed onto a salt porogen, then cooled down had an increase in hydroxyl % (carboxyl %). As shown in the embodiment in FIG. 8A, devices made from a polymer (e.g., PEEK) on a hot press (e.g., a hot press with a heating rate of approximately 100 to 200 degrees Celsius per minute) for four (4) minutes above 343 Celsius, and at a cooling rate of approximately 20 to 50 Celsius per minute with localized heating, showed an increase in hydroxyl/carboxyl % (as shown at "CageTop" and "CageBottom") over the body of the device or injected molded devices (e.g., "CageBulk" and "Injection Mold"). Further, devices made in an oven (e.g., an oven with a heating rate of about 10 to 20 degrees Celsius per minute) for about 45 minutes above 343 Celsius and then cooled at a rate of about 5 to 10 Celsius per minute.

FIG. 8B shows a bar graph representing hydroxyl group percentages for porous polymers cooled or recrystallized against different substrates, including salt (NaCl), $CaCl_2$, $CaBr_2$, $CaI_2$, Aluminum, and the hydroxyl group % of the polymer when a device is created through injection molding (e.g., without the processes described herein). As shown in the embodiment in FIG. 8B, it appears that the hydroxyl group % is relatively unchanged, regardless of the substrate used. This may contradict previous findings suggesting that substrates affect wettability.

FIG. 8C shows a bar graph representing hydroxyl group percentages of porous polymers recrystallized again various substrates with pressure applied and without pressure applied. As shown in the embodiment in FIG. 8C, the hydroxyl group percentage is increased with the use of salt in the process (e.g., "Pressure FlatSalt" and "No Pressure FlatSalt"), but potentially not as significantly as the heating and cooling process.

FIG. 8D shows a bar graph representing hydroxyl group percentages of porous polymers cooled at different rates (e.g., after heating as described herein). As shown in this embodiment, quenching, quenched then annealed, and slow cooling does not affect the hydroxyl/carboxyl % of the porous polymer after heating and processing as described herein.

FIG. 8E shows a bar graph depicting hydroxyl group percentages of porous polymers heated at two different temperatures (180 degrees Celsius and 340 degrees Celsius) with and without single crystal salt contact. In the embodiment shown in FIG. 8E, a sample of a porous polymer that is not in contact with salt (e.g., "Air") heated to about 180 degrees Celsius (via a hot plate) shows hydroxyl group percentages of about 25 to 40. In particular embodiments, the sample heated to 180 degrees Celsius, without salt contact, may have a hydroxyl group percentage of about 32.1 or about 27.5 to 36.7.

Continuing with the embodiment shown in FIG. 8E, a sample of porous polymer that is not in contact with salt (e.g., "Air") heated to about 340 degrees Celsius (via a hot plate) shows hydroxyl group percentages of about 45 to 65. In particular embodiments, the sample heated to 340 degrees Celsius, without salt contact, may have a hydroxyl group percentage of about 54.9 or about 48.1 to 61.7.

FIG. 8E further depicts a sample porous polymer that is contact with salt (e.g., "Salt") heated to about 180 degrees Celsius having hydroxyl group percentages of about 20 to 35. In one or more embodiments, the sample heated to about 180 degrees in contact with salt may have a hydroxyl group percentage of about 27.6 to about 22.4 to 32.8.

FIG. 8E also depicts a sample porous polymer that is contact with salt (e.g., "Salt") heated to about 340 degrees Celsius having hydroxyl group percentages of about 40 to 60. In one or more embodiments, the sample heated to about 340 degrees in contact with salt may have a hydroxyl group percentage of about 50.8 to about 42.9 to 58.7.

Exemplary Porous Layer Data

FIGS. 9A and 9B show porous layer data of an exemplary porous polymer (e.g., PEEK) produced in accordance with the processes described herein as measured with a direct distance transformation method from microcomputed tomography scans at a consistent threshold. As shown in the embodiment depicted in FIG. 9A, the porous layer includes a plurality of substantially spherical pores extending through the solid body for a defined distance (e.g., from 0.5899 mm to 0.8478 mm). In a particular embodiment, the pore layer thickness (e.g., the defined distance) is approximately 0.6911 mm. In particular embodiments, the porogen structure depends upon the shape of the porogen material and the arrangement of the porogen. Thus, the pores may be irregular (e.g., not in a defined pattern) or regular (in a defined pattern).

Continuing with the embodiment shown in FIG. 9A, the pores are separated by struts that define the shape of the pores. According to one embodiment, the strut spacing (e.g., pore size) is between about 0.2158 mm and 0.2355 mm. In a particular embodiment, the strut spacing is about 0.1 to 0.5 mm. In some embodiments, the strut thickness is between about 0.0945 mm and 0.1132 mm. In further embodiments, the strut thickness is between about 0.05 mm and 0.20 mm. In a particular embodiment, the strut spacing is approximately 0.2266 mm, and the strut thickness is approximately 0.1019 mm.

In the embodiment shown in FIG. 9B, the porosity of the porous layer is between 62.57% and 64.97%. In a particular embodiment, the porosity is approximately 63.59%. In a further embodiment, the porosity is approximately 0.1 to 65%. In one embodiment, interconnectivity between the pores is between 99.0754% and 99.981%, and in a particular embodiment, the interconnectivity is approximately 99.87%. In still further embodiments, the interconnectivity is about 40.0 to 99.9%. As will be understood by one of ordinary skill in the art, pore interconnectivity of approximately 99% indicates that substantially all pores are connected and all porogen has been leached/removed from the polymer (e.g., as described herein).

Exemplary Expulsion Force Data

FIG. 10 shows expulsion force data of an exemplary device including a porous polymer (e.g., PEEK) produced in accordance with the processes described herein. In various embodiments, as shown in FIG. 10, the expulsion force that may displace a device comprising a porous polymer as produced by processes discussed herein exceeds 150 N. In a particular embodiment, the expulsion force is at least 178 N and may be as high as 200 N, if the device also includes ridges in its porous surface structure. In contrast, in a particular embodiment, the expulsion force that may displace a device comprising an unprocessed polymer does not exceed 140 N and may be as low as 60 N. As will be understood by one of ordinary skill in the art, expulsion resistance (force, as measured in Newtons) is a function of a coefficient of friction and the normal force applied. Thus, devices with porous surfaces created by processes described herein should have similar expulsion resistance, regardless of the size or shape of the device.

Exemplary Use Cases

Materials created from the processes described herein may have a wide variety of uses. In particular embodiments, the processes described herein may be beneficial in any application where it is desired to adhere a material to the second material with different properties (e.g., adhere a first polymer with a first stiffness to a second polymer with a second stiffness). Such as, for example, adhering a soft polymer (e.g., polyethylene, polyvinyl-alcohol, or polycarbonate-urethane) to a harder polymer such as PEEK. This example may be applicable for knee or hip replacements. As a second example, porous polymers may be used in medical devices and more particularly for orthopedic applications to promote tissue ingrowth. Other exemplary uses may be aerospace, automotive, and other fields.

FIGS. 11A, 11B, and 11C show one non-limiting, exemplary embodiment of a medical device comprising the materials created from the processes described herein. As will be understood, the example is for discussion purposes only and should not be considered to be limiting of the types, shapes, sizes, etc. of devices that may be manufactured by the processes or have the features or properties described herein.

As shown in FIG. 11A, in a particular embodiment, the processes described herein are used to create a spinal implant 1101 that is hexahedral in shape with at least one porous layer. In one embodiment, the spinal implant 1101 comprises two substantially square-shaped porous faces that are substantially parallel to one another with one convexly-curved side 1103, as shown in FIG. 11A. In a particular embodiment, as shown in FIGS. 11B and 11C, the two porous faces, 1109 and 1113, are angled slightly inwards towards each other. Between the two porous faces is a body layer 1111 of varying thicknesses. Returning to FIG. 11A, the spinal implant 1101 may include an inner void 1105 that is in substantially the same shape as the two porous faces and extends from the surface (e.g., 1115) of one of the porous faces (e.g., 1109) through the surface (e.g., 1119) of the other porous face (e.g., 1113).

As will be appreciated by one having ordinary skill in the art, the spinal implant may be produced in different sizes and shapes to accommodate different patients, implant locations, etc. (e.g., larger implants for patients with larger anatomies, smaller implants for patients with smaller anatomies, larger implants for use in the lumbar vertebrae, smaller implants for use in the thoracic vertebrae, etc.). Similarly, although not shown in the figures, the spinal implant may be substantially cylindrical in shape, substantially cubic in shape, substantially rectangular in shape with a pyramidal nose, substantially half-moon in shape, substantially solid with no voids, substantially hollow with multiple voids of varying shapes and sizes, include ridges on the porous surfaces of varying widths and heights, etc.

As will be understood by one of ordinary skill in the art, the spinal implant (or other device) may be made from a radiolucent material, such as PEEK. Thus, according to one embodiment, as shown in FIGS. 11A, 11B, and 11C, the spinal implant further includes one or more markers 1107 for detection of tissue ingrowth (e.g., bone) into the implant. For example, in one embodiment, the implant may include two tantalum markers 1107 that are substantially-cylindrical in shape (these markers, however, may be any suitable shape, such as rectangular, triangular, conical, etc.). Generally, the markers are positioned so that they extend vertically through the implant with the circular end-surfaces of the marker, 1117 and 1121, substantially flush with the top of porous faces, 1115 and 1119, as shown in FIGS. 11B and 11C. In another embodiment, although not shown, the end-surfaces of the marker, 1117 and 1121, are angled so that they are even with the top of porous faces, 1115 and 1119. Thus, to determine tissue ingrowth, radiography or another electro-magnetic-imaging technique is used to take a lateral view of the implanted spinal implant. By determining the position of the ends of the markers, 1117 and 1121, in the image and comparing them to the location of the edges of the tissue in the image, the amount of tissue ingrowth may be determined. Specifically, because the ends of the markers, 1117 and 1121, are at the edges of the porous surface of the spinal implant, 1115 and 1119, any tissue that extends past the ends of the markers should represent tissue ingrowth into the spinal implant. As will be appreciated by one having ordinary skill in the art, multiple images of the same spinal implant taken at different times may be compared to determine the change in tissue ingrowth, rate of tissue ingrowth, etc.

Further, as will be understood by one having ordinary skill in the art, a marker (e.g., marker 1107) may be of any suitable material or construction. In various embodiments, the marker may be made of a radiolucent material, but include a radiopaque additive (e.g., barium sulfate or bismuth compounds). In one or more embodiments, the marker may be made form a suitable radiopaque metal.

Because the amount of tissue ingrowth may be determined, a strength of the bond between the tissue and an implant may be calculated/inferred (e.g., any orthopedic implant, including, for example, the implant described above). In various embodiments, this could be used to determine, based on amount of measurable tissue ingrowth, when a person with a spinal implant may be able to safely resume load-bearing activities.

In various embodiments, as described above, a clinician may be instructed to take a radiograph of a spinal implant that includes the above described markers and porous layer. The clinician may be further instructed to measure the distance the tissue has grown into the implant, based on the distance the tissue has grown past the top (or bottom) of the markers. In this way, the distance the tissue has grown past the markers may be correlated to a strength of adhesion of the implant to the surrounding tissue (e.g., bone), which may give an indication of when the person with the implant may be able to perform certain activities, with a lower risk of further injury.

Conclusion

The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope.

What is claimed is:

1. A method for generating a medical device that promotes tissue ingrowth, the method comprising:
   heating a surface of a solid piece of polymer to a processing temperature below a melting point of the polymer;
   holding the processing temperature while applying pressure to displace a porogen layer through the surface of the polymer to create a matrix layer comprising the polymer and the porogen layer; and
   removing at least a portion of the porogen layer from the matrix layer thereby forming the medical device comprising at least a portion of the solid piece of the polymer with a porous layer.

2. The method of claim 1, wherein the at least a portion of the solid piece of the polymer is integrally and directly connected with the porous layer.

3. The method of claim 1, wherein the porous layer comprises a first percentage of hydroxyl groups that is greater than a second percentage of hydroxyl groups in the solid piece of polymer.

4. The method of claim 1, wherein the porous layer comprises a first carbon to oxygen atomic ratio that is substantially identical to a second carbon to oxygen atomic ratio of the solid piece of the polymer.

5. The method of claim 1, wherein the porous layer comprises a first wettability that is greater than the second wettability of the solid piece of the polymer.

6. The method of claim 1, wherein removing at least a portion of the porogen layer from the matrix layer comprises removing substantially all of the porogen layer.

7. The method of claim 1, wherein the porous layer comprises a plurality of pores that is substantially spherical and in an irregular distribution pattern.

8. The method of claim 1, wherein the polymer comprises a thermoplastic polymer.

9. The method of claim 1, wherein the porosity of the porous layer is between about 61% to about 66%.

10. The method of claim 1, wherein the interconnectivity of the porous layer is about 99%.

11. The method of claim 1, wherein an interfacial shear strength between the at least a portion of the solid piece of the polymer and the porous surface layer of the medical device is at least about 17 MPa.

12. A method for generating a medical device that promotes tissue ingrowth, the method comprising:
heating a surface of a solid piece of polymer to a processing temperature below a melting point of the polymer;
holding the processing temperature while applying pressure, for a processing time, to displace a porogen layer through the surface of the polymer into the solid piece of polymer by a defined distance to create a matrix layer comprising the polymer and the porogen layer;
removing the applied pressure and heat and cooling the surface of the solid piece of polymer at a predetermined rate; and
removing the porogen layer from the matrix layer thereby forming the medical device comprising at least a portion of the solid piece of the polymer directly connected with a porous layer.

13. The method of claim 12 further comprising, prior to holding the processing temperature while applying pressure for the processing time, determining the processing time based on a desired interfacial shear strength of the medical device.

14. The method of claim 12, wherein an interfacial shear strength of the medical device increases substantially linearly with increase of the processing time.

15. The method of claim 12, wherein the porous layer comprises a first percentage of hydroxyl groups that is greater than a second percentage of hydroxyl groups in the solid piece of polymer.

16. The method of claim 12, wherein the porous layer comprises a first carbon to oxygen atomic ratio that is substantially identical a second carbon to oxygen atomic ratio of the solid piece of the polymer.

17. The method of claim 12, wherein the porous layer comprises a first wettability that is greater than the second wettability of the solid piece of the polymer.

18. The method of claim 12, wherein the porosity of the porous layer is between about 61% to about 66% and the interconnectivity of the porous layer is about 99%.

19. The method of claim 12, wherein an interfacial shear strength between the at least a portion of the solid piece of the polymer and the porous surface layer of the medical device is at least about 17 MPa.

20. A method for generating a medical device that promotes tissue ingrowth, the method comprising:
heating a surface of a solid piece of polymer to a processing temperature below a melting point of the polymer;
holding the processing temperature while applying pressure to displace a porogen layer through the surface of the polymer to create a matrix layer comprising the polymer and the porogen layer; and
removing at least a portion of the porogen layer from the matrix layer thereby forming the medical device comprising at least a portion of the solid piece of the polymer with a porous layer, wherein the porous layer comprises a first percentage of hydroxyl groups that is greater than a second percentage of hydroxyl groups in the solid piece of polymer, and wherein the porous layer comprises a first wettability that is greater than the second wettability of the solid piece of the polymer.

* * * * *